United States Patent [19]

Pirl et al.

[11] Patent Number: 5,100,610

[45] Date of Patent: Mar. 31, 1992

[54] TUBE PLUG INSPECTION SYSTEM

[75] Inventors: William E. Pirl, Levelgreen; Edward A. Ray, Plum Boro Allegheny Co.; Annette M. Costlow, Trafford; Charles H. Roth, Jr., N. Huntingdon; Francis X. Gradich, Elizabeth Twp. Allegheny Co.; David A. Chizmar, Washington Twp. Westmoreland Co., all of Pa.

[73] Assignee: Westinghouse Electric Corp., Pittsburgh, Pa.

[21] Appl. No.: 616,444

[22] Filed: Nov. 20, 1990

[51] Int. Cl.⁵ .......................................... G21C 17/02
[52] U.S. Cl. .................................. 376/260; 376/250; 376/245; 376/310
[58] Field of Search ................ 376/250, 245, 260, 310

[56] References Cited

U.S. PATENT DOCUMENTS

| | | | |
|---|---|---|---|
| 3,831,084 | 8/1974 | Scalese et al. | 324/40 |
| 4,079,701 | 3/1978 | Hickman et al. | 122/382 |
| 4,134,067 | 1/1979 | Woodbury | 324/219 |
| 4,385,297 | 5/1983 | Schmitt et al. | 340/870.31 |
| 4,390,042 | 6/1983 | Kucherer et al. | 138/89 |
| 4,616,258 | 10/1986 | Ono et al. | 358/100 |
| 4,625,165 | 11/1986 | Rothstein | 324/220 |
| 4,690,006 | 9/1987 | Urata | 73/866.5 |
| 4,772,849 | 9/1988 | Tedder | 324/220 |
| 4,856,337 | 8/1989 | Metala et al. | 73/601 |
| 5,025,215 | 6/1991 | Pirl | 324/220 |
| 5,028,381 | 7/1991 | Dugue | 376/252 |

*Primary Examiner*—Brooks H. Hunt
*Assistant Examiner*—Frederick H. Voss
*Attorney, Agent, or Firm*—Walter S. Stevens

[57] ABSTRACT

System for inspecting the interior of tube plugs, particularly tube plugs of the type having expander elements disposed therein. The system includes a probe assembly connectable to the tube plug, the probe assembly having a rotatable and translatable probe carrier housing for housing a sensor probe capable of inspecting the tube plug. The probe assembly also includes a leaf spring extending through the probe carrier housing and attached to the sensor probe for radially outwardly biasing the sensor probe into sensing contact with the interior of the tube plug, particularly the interior of the tube plug located between the top of the tube plug and the expander element. A tangle-free flexible hose is connected at one end thereof to the probe carrier housing for transversely rotating and longitudinally translating the probe carrier housing. The flexible hose is also connected at the other end thereof to a probe driver assembly that rotates the flexible hose which in turn rotates the probe carrier housing. Rotation of the probe carrier housing rotatably translates the probe carrier housing into the tube plug for inspecting the tube plug in a helical scanning pattern.

19 Claims, 13 Drawing Sheets

TUBE PLUG INSPECTION SYSTEM

BACKGROUND

This invention relates to apparatus for inspecting tubular members and more particularly relates to a system for inspecting hollow tube plugs installed in nuclear steam generators.

Before discussing the current state-of-the-art, it is beneficial first to briefly describe the structure and operation of a typical nuclear steam generator. In this regard, a typical nuclear steam generator comprises a vertically oriented shell and a plurality of U-shaped heat transfer tubes disposed in the shell. Pressurized radioactive primary fluid (e.g., water), which is heated by a nuclear reactor core, flows through the tubes as non-radioactive secondary fluid (i.e., water) of lower temperature circulates around the tubes. Heat is transferred from the primary fluid to the secondary fluid for producing steam in a manner well known in the art of nuclear-powered steam production. Such a nuclear steam generator is disclosed in U.S. Pat. No. 4,079,701 entitled "Steam Generator Sludge Removal System" issued Mar. 21, 1978 to Robert A. Hickman et al.

It is important that the radioactive primary fluid remains separated from the non-radioactive secondary fluid so that the secondary fluid is not radioactively contaminated by the primary fluid. Contamination of the secondary fluid by the primary fluid may lead to excessive release of radioactivity to the environment. Excessive release of radioactivity to the environment is undesirable from a health and safety standpoint. Therefore, it is important that the tubes disposed in the steam generator remain leak-tight so that the radioactive primary fluid will not commingle with and contaminate the non-radioactive secondary fluid.

Occasionally, however, some of the tubes may experience degradation and may develop through-wall cracks due, for example, to stress corrosion cracking. These through-wall cracks may lead to commingling of the radioactive primary fluid with the non-radioactive secondary fluid. Therefore, the tubes are periodically inspected to identify those tubes suspected of being degraded or of having through-wall cracks. Heat transfer tubes suspected of being degraded or of having cracks are typically either sleeved or plugged, in a manner well known in the art, so that the primary fluid will not commingle with the secondary fluid. When a degraded tube is sleeved, a tubular sleeve is inserted into the tube and secured thereto, such as by welding, so that the degraded portion of the tube wall is covered. On the other hand, when a degraded tube is plugged, a tubularly-shaped hollow tube plug is inserted into one or both open ends of the tube so that radioactive primary fluid will not enter the degraded tube. Thus, in the case either of sleeving or plugging, the primary fluid is prevented from commingling with the secondary fluid even though the tube is degraded or cracked.

With respect to tube plugs, one type of tube plug suitable for use in nuclear steam generator heat transfer tubes is disclosed in U.S. Pat. No. 4,390,042 entitled "Tube Plug" issued June 28, 1983 to Harvey D. Kucherer et al. This type of tube plug comprises a shell having a closed top end and an open bottom end and having a tapered inner surface against which an externally tapered expander member moves by application of a pulling force. The expander member is drawn from the closed end to the open end of the shell. The motion of the expander member relative to the shell causes the shell to expand into contact with the heat transfer tube thereby plugging the tube.

However, the tube plug itself may become degraded and develop through-wall cracks. In this regard, it has been observed that the upper wall section of the tube plug is susceptible to stress corrosion cracking as a result of the substantial tensile stresses applied to the upper region of the walls of the tube plug by the expander member when it is drawn from the closed end to the open end of the tube plug. Such substantial stresses may eventually lead to through-wall cracks. A tube plug that is cracked may allow the primary fluid to enter the degraded tube in which the tube plug is disposed. If this occurs, there will be an increased risk that the radioactive primary fluid will commingle with the non-radioactive secondary fluid. In addition, if through-wall cracks develop in the upper region of the walls of the tube plug, there is a risk that the top of the tube plug will separate from the remainder of the tube plug and become a high-velocity projectile in the heat transfer tube. That is, the pressure of the primary fluid acting against the tube plug could under certain conditions separate and propel the degraded top portion of the tube plug upwardly within the heat transfer tube and damage the heat transfer tube, particularly in the U-bend region of the tube. Such severe damage to the tube may cause a breach of the tube wall. This is undesirable from a safety standpoint because such a breach could lead to commingling of the radioactive primary fluid with the non-radioactive secondary fluid. Consequently, it is desirable to inspect the upper wall section of the tube plug between the top of the tube plug and the top of the expander member to determine if this region is degraded or cracked.

However, the expander member presents an obstacle to inspecting the upper interior region of the tube plug located between the top of the tube plug and the expander member. Therefore, a problem in the art is to inspect the upper interior region of the tube plug located between the top of the tube plug and the expander member even though the expander member may hamper access to that region of the tube plug.

Probe devices for inspecting tubularly-shape members are known. For example, an electro-mechanical eddy current probe having a rotatable sensing head for sensing the wall thickness of and locating local defects in a tube or conduit through which it is passed is disclosed in U.S. Pat. No. 4,625,165 entitled "Tube Inspection Probe With Rotating Eddy Current Coil", issued Nov. 25, 1986 to Samuel Rothstein. Although this patent may disclose an electro-mechanical eddy current probe, this patent does not appear to disclose a system capable of inspecting the upper interior region of a tube plug having an expander member disposed therein.

A probe for longitudinally traversing and circumferentially inspecting the interior of a tube is disclosed in U.S. Pat. No. 4,772,849 entitled "Rotating Probe Head For Tube Inspection" issued Sept. 20, 1988 to Joseph A. Tedder. Although this patent may disclose a probe for inspecting the interior of a tube, this patent does not appear to disclose a system capable of inspecting the upper interior region of a tube plug having an expander member disposed therein.

Thus, although the above recited patents may disclose apparatus for inspecting tubularly-shape members, these patents do not appear to disclose a system for inspecting the upper interior region of a tube plug having an expander member disposed therein.

Consequently, what is needed is a system for inspecting a tube plug having an expander member disposed therein, wherein the system is capable of inspecting the upper interior region of the tube plug between the top of the tube plug and the top of the expander member.

SUMMARY

Disclosed herein is a system for inspecting the upper interior region of tube plugs, particularly hollow tube plugs of the type having a tapering inner wall defining a tapered cavity and having an exteriorly tapered expander member disposed in the cavity. The expander member of such a tube plug has a narrow threaded bore therethrough for receiving a threaded push-rod tool for longitudinally moving the expander member such that the expander member slidably engages the tapered inner wall. As the expander member is moved, the outer walls of the tube plug expand radially outwardly to engage the inner surface of the heat transfer tube for plugging the tube.

In general, the inspection system of the present invention comprises probe means connectable to the tube plug for extending an inspection sensor probe therefrom through the narrow bore of the expander member for inspecting the upper interior region of the tube plug located between the top of the expander member and the top of the tube plug. The system further comprises rotatable hose means connected to the probe means for transversely rotating the sensor probe and for longitudinally translating the sensor probe as the sensor probe inspects the tube plug. Moreover, the system further comprises drive means engaging the hose means for rotating the hose means and for extending the sensor probe into sensing contact with the inner wall of the tube plug.

More particularly, the probe means of the invention comprises a probe carrier housing for housing the sensor probe and for carrying the sensor probe into the tube plug. The probe carrier housing has a slot through the top portion thereof and also has external threads therearound for engaging internal threads belonging to an elongated extension member which surrounds the probe carrier housing. The probe carrier housing is sized to pass through the narrow bore of the expander member. The extension member is sized not to pass through the narrow bore of the expander, but rather to abut against the bottom of the expander member for reasons provided hereinbelow.

The probe means further comprises a first collar surrounding the extension member, the first collar having a depending shoulder for abutting the open end of the tube plug. Also surrounding the extension member and spaced-apart from the first collar is a second collar. Connecting the first collar and the second collar are a pair of guides each having an end thereof anchored in the first collar and each having the other end thereof slidably received through the second collar. Moreover, surrounding the extension member and interposed between the first collar and the second collar is a compressible spring member for maintaining the first collar and the second collar in a spaced-apart relationship and for biasing the first collar into abutment against the open end of the tube plug. Surrounding the extension member and attached thereto is a rotator for rotating the probe carrier housing. The rotator has a bore therein for slidably receiving an actuator. Attached to the actuator is a resilient leaf spring, which extends from the actuator, through the probe carrier housing to adjacent the slot formed in the probe carrier housing. The top portion of the leaf spring is bent at a predetermined angle and has a cam surface thereon for reasons disclosed hereinbelow. Attached to the bent portion of the leaf spring is the sensor probe. Moreover, attached to the interior of the probe carrier housing adjacent the bent portion of the leaf spring is a cam for slidably engaging the cam surface belonging to the leaf spring.

The hose means of the invention comprises a flexible, segmented, and hollow hose having a flexible cable extending therethrough. Connecting adjacent segments of the segmented hose is a connector configured for maintaining the hose in a tangle-free state. The hose has one end connected to the rotator and the other end connected to the drive means. Moreover, one end of the cable is attached to the actuator and the other end of the cable is connected to the drive means.

During operation of the inspection system the probe means is coaxially aligned with the tube plug. The probe means is axially translated such that the shoulder belonging to the first collar abuts the open end of the tube plug. As the probe means continues to be axially translated, the distance between the first collar and the second collar decreases as the spring member therebetween compresses. Moreover, as the probe means continues to be axially translated, the extension member enters the tube plug and abuts the bottom of the expander member.

As the system operates, the drive means rotates the cable which in turn rotates the rotator. The rotator rotates the probe carrier housing to threadably engage the external threads of the probe carrier housing with the internal threads of the extension member. The probe carrier housing thus threadably advances through the extension member as the probe carrier housing is rotated. As the probe carrier housing advances through the extension member it also advances through the narrow bore formed in the expander member because the probe carrier housing is sized to pass through the narrow bore of the extension member.

The drive means is also operated to pull the cable connected to the actuator. As the cable is pulled, the actuator is moved which also moves or pulls the leaf spring. As the leaf spring is pulled, the cam surface belonging to the bent portion thereof slides across the cam disposed in the probe carrier housing. As the cam surface slides across the cam, the top portion of the leaf spring is deflected flexibly radially outwardly through the slot formed through the top portion of the probe carrier housing. Of course, the sensor probe is connected to the top portion of the leaf spring; therefore, the sensor probe is also radially outwardly moved as the top portion of the leaf spring is deflected flexibly radially outwardly. After the tube plug is inspected, the top portion of the leaf spring is deflected flexibly radially inwardly through the slot formed through the top portion of the probe carrier housing in a manner substantially the reverse of its outward movement. As the top portion of the leaf spring is deflected inwardly, the sensor probe is thereby withdrawn into the probe carrier housing for protecting the sensor probe from damage. According to the present invention, the sensor probe is both transversely rotated and longitudinally translated to inspect the inner wall of the tube plug along a helical path having a pitch equal to the pitch of the external threads of the probe carrier housing or the internal threads of the extension member. Moreover, in the manner summarized hereinabove, the inspection system extends the sensor probe radially outwardly from the probe carrier housing to inspect the inner wall of the tube plug and retracts the sensor probe radially inwardly into the probe carrier housing to protect the sensor probe from damage.

An object of the invention is to provide a system for inspecting the upper interior portion of a hollow tube plug of the type having an expander member disposed therein, the expander member having a narrow bore therethrough, wherein the expander member hampers access to the upper interior portion of the tube plug.

A feature of the invention is the provision of a drive means for simultaneously rotating and translating a sensor probe through the narrow bore of the expander member for helically scanning the upper portion of the tube plug.

An advantage of the invention is that the inspection system will inspect the upper interior portion of a hollow tube plug having an expander member disposed therein.

BRIEF DESCRIPTION OF THE DRAWINGS

While the specification concludes with claims particularly pointing out and distinctly claiming the subject matter of the invention, it is believed the invention will be better understood from the following description taken in conjunction with the accompanying drawings, wherein:

DETAILED DESCRIPTION OF THE PREFERRED EMBODIMENT(S)

Figure 1:
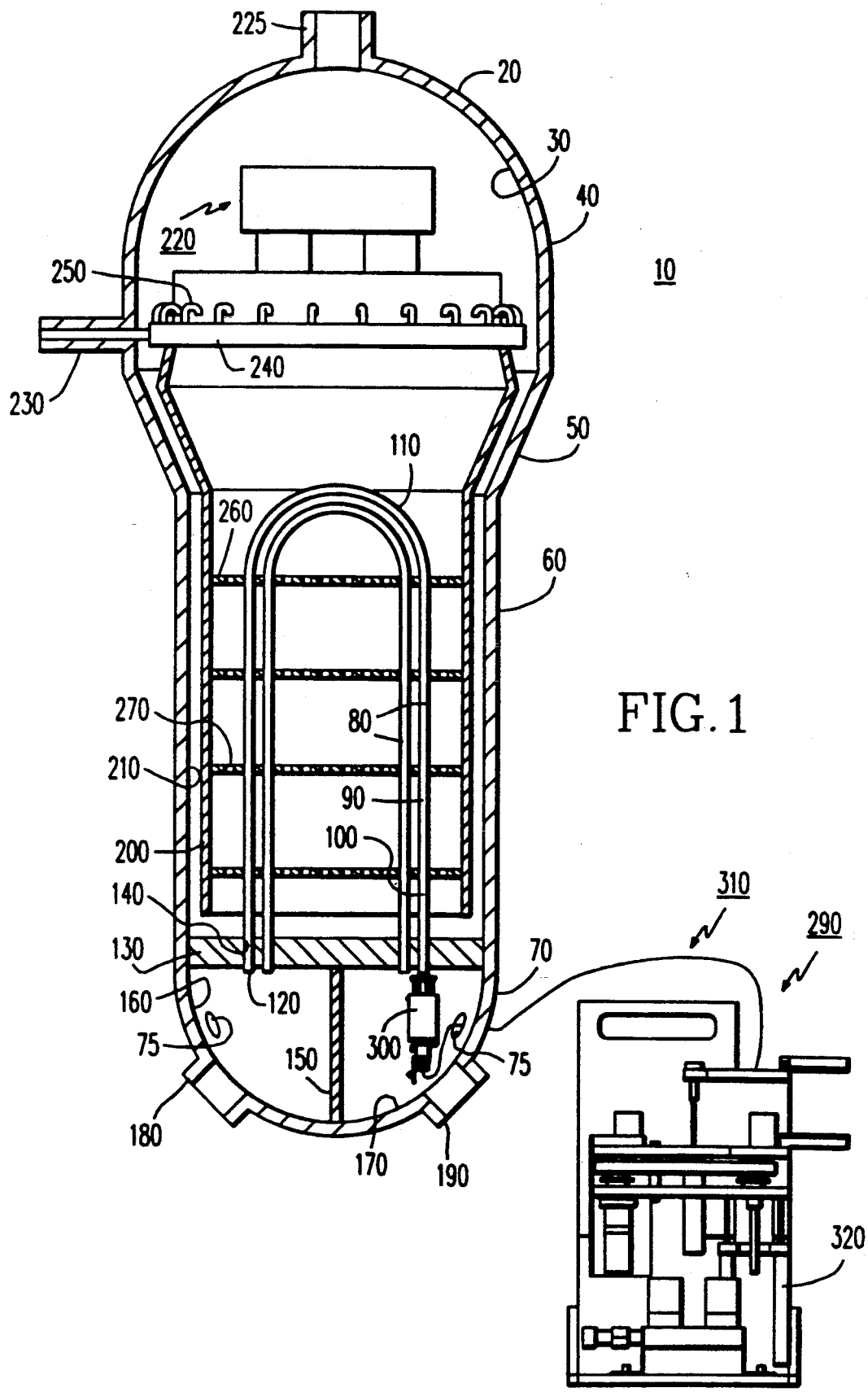
FIG. 1 is a view in partial vertical section of a typical nuclear steam generator, with parts removed for clarity, showing a plurality of heat transfer tubes disposed therein and is also a view of the system of the invention connected to one of the heat transfer tubes.

In a nuclear steam generator, it is important for safety reasons that the radioactive primary fluid remains separated from the non-radioactive secondary fluid so that the secondary fluid is not radioactively contaminated by the primary fluid. Therefore, it is important that the heat transfer tubes disposed in the steam generator remain leak-tight so that the radioactive primary fluid will not commingle with and contaminate the non-radioactive secondary fluid. Occasionally, such tubes become degraded and develop cracks. When a heat transfer tube is suspected of being degraded or of having through-wall cracks, a tube plug may be installed into the tube to prevent the primary fluid from commingling with the secondary fluid. However, the tube plug itself may become degraded and may develop cracks, especially in the upper interior region thereof. Therefore, it is desirable to inspect any tube plugs suspected of being degraded or cracked to determine whether they have in fact become degraded or cracked. Disclosed herein is a system for inspecting a tube plug to determine if the tube plug is degraded or has developed cracks, especially in the upper interior region thereof.

Before describing the preferred embodiment of the present invention, it is instructive to first describe the structure and operation of a typical nuclear steam generator. Therefore, referring to FIG. 1, there is shown a nuclear steam generator, generally referred to as 10, for generating steam. Steam generator 10 comprises a vertically-oriented shell 20 defining a cavity 30 therein. Shell 20 has a dome-shaped upper shell portion 40, a frusto-conical transition portion 50 integrally attached to upper shell portion 40, a cylindrical hull portion 60 integrally attached to transition portion 50, and a bowl-shaped lower shell portion 70 integrally attached to hull portion 60. Formed through lower shell portion 70 are a plurality of manway openings 75 (only one of which is shown) for reasons provided hereinbelow. Of course, manway openings 75 are capable of being sealingly covered by suitable manway covers (not shown).

Still referring to FIG. 1, disposed in cavity 30 are a plurality of vertically-oriented U-shaped steam generator tubes 80 for conducting radioactive primary fluid (e.g., water) therethrough, the plurality of tubes 80 defining a tube bundle 90. Each tube 80 has an inner wall 95 (see FIG. 2). Moreover, as shown in FIG. 1, each U-shaped tube 80 has a pair of vertical tube leg portions 100 interconnected by a U-bend tube portion 110 integrally formed therewith. In addition, each tube leg portion 100 has an open tube end 120 for passage of the primary fluid therethrough. Disposed in cavity 30 near lower shell portion 70 is a horizontal tube sheet 130 having a plurality of apertures 140 therethrough for receiving and for vertically supporting each tube end 120.

Referring again to FIG. 1, disposed in lower shell portion 70 is a vertical divider plate 150 for dividing lower shell portion 70 into an inlet plenum chamber 160 and an outlet plenum chamber 170. Manway opening 75 allows for access to inlet plenum chamber 160 and outlet plenum chamber 170. Integrally attached to lower shell portion 70 is an inlet nozzle 180 and an outlet nozzle 190 in communication with inlet plenum chamber 160 and outlet plenum chamber 170, respectively. Disposed in cavity 30 above tube sheet 130 and interposed between shell 20 and tube bundle 90 is a cylindrical wrapper sheet 200 defining an annular downcomer region 210 between shell 20 and wrapper sheet 200. Wrapper sheet 200 is open at its bottom end and partially closed at its top end. That is, formed through the top end of wrapper sheet 200 are a plurality of holes (not shown) in its top end for passage of a steam-water mixture therethrough. Mounted atop wrapper sheet 200 is a moisture separator assembly, generally referred to as 220, for separating the steam-water mixture into liquid water and relatively dry saturated steam. Moisture separator assembly 220 also has holes (not shown) in the bottom portion thereof for receipt of the steam-water mixture from the interior of wrapper sheet 200 and holes (not shown) in the top portion thereof for passage of the dry saturated steam flowing upwardly from moisture separator assembly 220. In addition, integrally attached to the top of upper shell portion 40 is a main steam line nozzle 225 for passage of the dry saturated steam therethrough after the dry saturated steam passes upwardly from moisture separator assembly 220.

As shown in FIG. 1, integrally attached to upper shell portion 40 is a feedwater nozzle 230 for passage of feedwater into a torodial feedring 240 which is in fluid communication with feedwater nozzle 230. Feedring 240 surrounds wrapper sheet 200 at the upper portion of wrapper sheet 200 and has a plurality of nozzles 250 attached thereto for passage of the feedwater from feedring 240, through nozzles 250 and downwardly into downcomer region 210. Disposed inwardly of wrapper sheet 200 are a plurality of horizontal spaced-apart tube support plates 260 (only four of which are shown) having holes 270 therethrough for receiving each tube 80 so that each tube 80 is laterally supported thereby. Each support plate 260 also has a plurality of orifices (not shown) therethrough for upward passage of the secondary fluid.

During operation of steam generator 10, the primary fluid, which is heated by a nuclear reactor core (not shown), flows from the reactor core through inlet nozzle 180 and into inlet plenum chamber 160. The primary fluid then travels through one of the open tube ends 120, through tubes 80, out the other open tube end 120 and into outlet plenum chamber 170, whereupon the primary fluid exits steam generator 10 through outlet nozzle 190. As the primary fluid flows through tubes 80, feedwater simultaneously enters steam generator 10 through feedwater nozzle 230. The feedwater then enters feedring 240, flows through nozzles 250 and flows downwardly through downcomer region 210 until the feedwater impinges tube sheet 130. The feedwater then turns upwardly to surround tube bundle 90. As the primary fluid flows through tubes 80 it gives up its heat to the secondary feedwater fluid surrounding tube bundle 90. A portion of the secondary feedwater fluid surrounding tube bundle 90 is converted into a steam-water mixture that flows upwardly to moisture separator assembly 220 which separates the steam-water mixture into liquid water and relatively dry saturated steam. The liquid water returns downwardly to bundle 90 as the dry saturated steam travels upwardly to exit steam generator 10. The dry saturated steam exits steam generator 10 through main steam line nozzle 280 and is transported to a turbine-generator (not shown) for producing electricity in a manner well known in the art of nuclear-powered electricity production. Such a steam generator is disclosed in U.S. Pat. No. 4,079,701 entitled "Steam Generator Sludge Removal System" issued Mar. 21, 1978 to Robert A. Hickman et al., the disclosure of which is hereby incorporated by reference.

Referring again to FIG. 1, there is illustrated the subject matter of the present invention, generally referred to as 290, which is a system for inspecting a tubularly-shaped member or tube plug for degradation or cracks. As described in more detail hereinbelow, inspection system 290 generally comprises probe means (e.g., a probe assembly 300) for extending an inspection probe sensor into the tube plug, hose means 310 connected to probe assembly 300 for transversely rotating and longitudinally translating the sensor probe, and drive means 320 connected to hose means 310 for operating hose means 310. Of course, it will be understood that before inspection system 290 is positioned to inspect the tube plug, the primary and secondary fluids are drained from steam generator 10 and a manway cover (not shown) is removed from manway opening 75 to allow access to inlet plenum chamber 160 and/or outlet plenum chamber 170.

Figure 2:
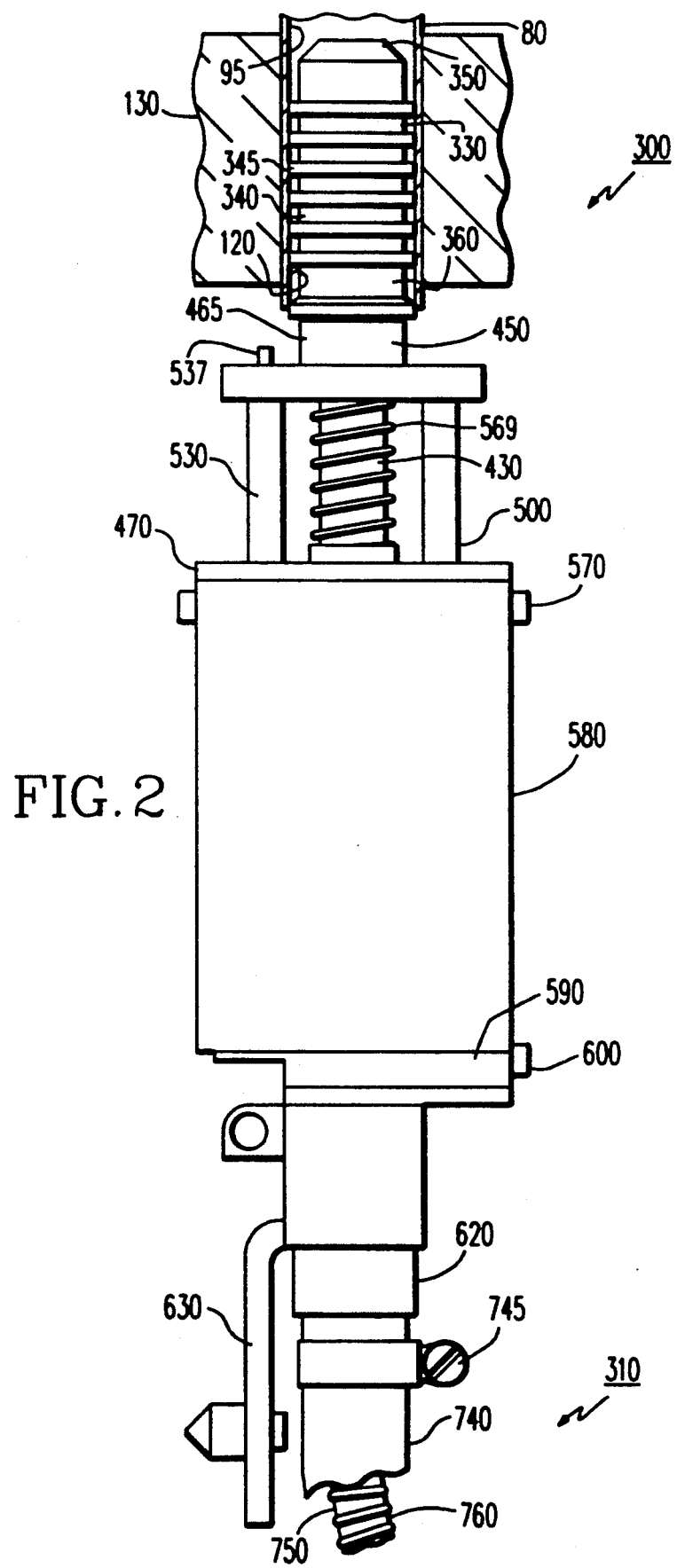
FIG. 2 is a view in partial vertical section showing a tube plug inserted into one of the tubes and showing probe means belonging to the system of the invention connected to the tube plug for inspecting the tube plug.
Figure 3:
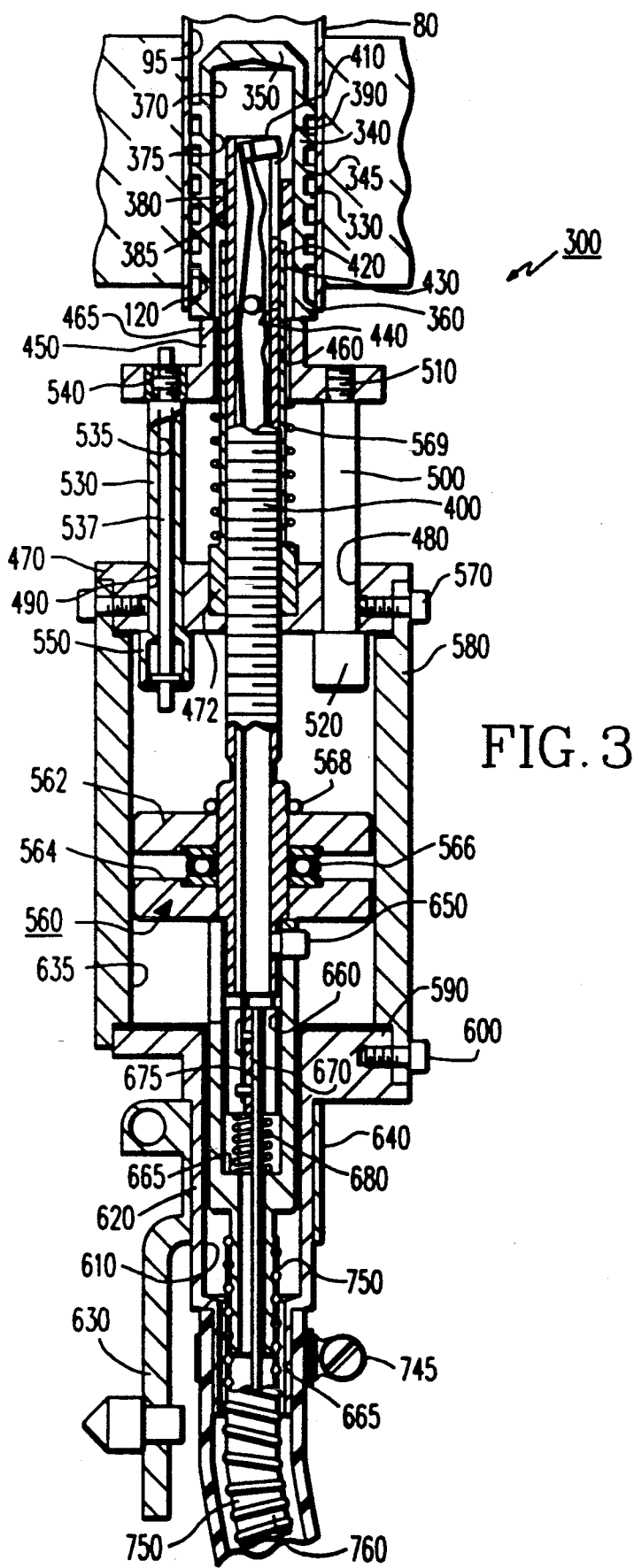
FIG. 3 is a view in partial vertical section of the probe means operatively disposed for inspecting the tube plug.

Turning now to FIGS. 2 and 3, the probe means, (e.g., probe assembly 300) is there shown in operative condition to inspect a tube plug 330 which is disposed in open end 120 of tube 80. Tube plug 330 may be made of "INCONEL" or the like for resisting stress corrosion cracking. Tube plug 330, which forms no part of the present invention, comprises a cylindrical shell 340 having a plurality of lands 345 extending therearound and integrally attached thereto for sealingly engaging inner wall 95 of tube 80. Shell 340 has a closed distal top end 350 and an open proximal bottom end 360. Moreover, shell 340 defines a chamber 370 therein that has a wall 375 gently tapering from closed distal top end 350 to near open proximal bottom end 360. Disposed in chamber 360 is a generally cylindrical externally tapered expander element 380 for expanding shell 340 into sealing engagement with inner wall 95 so that tube 80 is plugged thereby. Expander element 380 has a narrow threaded bore 385 longitudinally therethrough for reasons provided hereinbelow. Prior to expanding shell 340 into sealing engagement with inner wall 95, expander element 380 is disposed nearer to closed distal top end 350 than to open proximal bottom end 360. Therefore, in order to expand shell 340 into sealing engagement with inner wall 95, a threaded pull-rod tool (not shown) is caused to engage threaded bore 385 of expander element 380 to pull expander element 380 from near distal top end 350 to near proximal bottom end 360. As expander element 380 is drawn toward proximal bottom end 360 it engages tapering wall 375, thereby causing shell 340 to radially outwardly expand into sealing engagement with inner wall 95. Such a tube plug 330 is fully disclosed in U.S. Pat. No. 4,390,042 issued June 23, 1983 in the name of Harvey D. Kucherer et al. and entitled "Tube Plug", the disclosure of which is hereby incorporated by reference.

Referring to FIGS. 2, 3, 4 and 5, probe assembly 300 comprises an elongated generally cylindrical probe carrier housing 390 having external threads 400 therearound and a longitudinal slot 405 therethrough near the distal end thereof. As described more fully hereinbelow, probe carrier housing 390 is sized to be inserted through the open proximal end 360 of tube plug 330 and through narrow bore 385 defined by expander element 380. It is important that probe carrier housing 390 be capable of extending through narrow bore 385. Probe carrier housing 390 should be capable of extending through narrow bore 385 so that the upper interior region of tube plug 330 between expander element 380 and distal top end 350 of tube plug 330 can be inspected. Probe carrier housing 390 has a sensor probe 410, such as a pancake-type eddy current coil, disposed therein for inspecting the portion of tube plug 330 between closed distal end 350 and expander element 380. A pancake-type eddy current coil suitable for use with the present invention is disclosed in U.S. patent application Ser. No. 079,860 filed July 30, 1987 in the name of Michael J. Metala and entitled "Apparatus and Method For Providing A Combined Ultrasonic And Eddy Current Inspection Of A Metallic Body", the disclosure of which is hereby incorporated by reference. Extending from sensor probe 410 is an electrically conductive wire 415 connected to sensor probe 410 at one end thereof and to a signal analyzer (not shown) at the other end thereof. The inspection signal is conducted through wire 415 to the analyzer where the inspection signal is analyzed to determine if tube plug 330 is degraded or cracked. Probe carrier housing 390 houses sensor probe 410 to protect probe 410 from damage in the manner disclosed hereinbelow and to assist in carrying sensor probe 410 into tube plug 330.

As illustrated in FIGS. 2 and 3, probe assembly 300 further comprises limit means 420 connected to probe carrier housing 390 for delimiting the length of the interior of tube plug 330 to be inspected. Limit means 420 comprises a generally cylindrical extension member 430 surrounding probe carrier housing 390. Extension member 430 defines a passage 440 therethrough having internal threads (not shown) for threadably engaging external threads 400 of probe carrier housing 390. Moreover, passage 440 has an open end for passage of probe carrier housing 390 therethrough.

Figure 4:
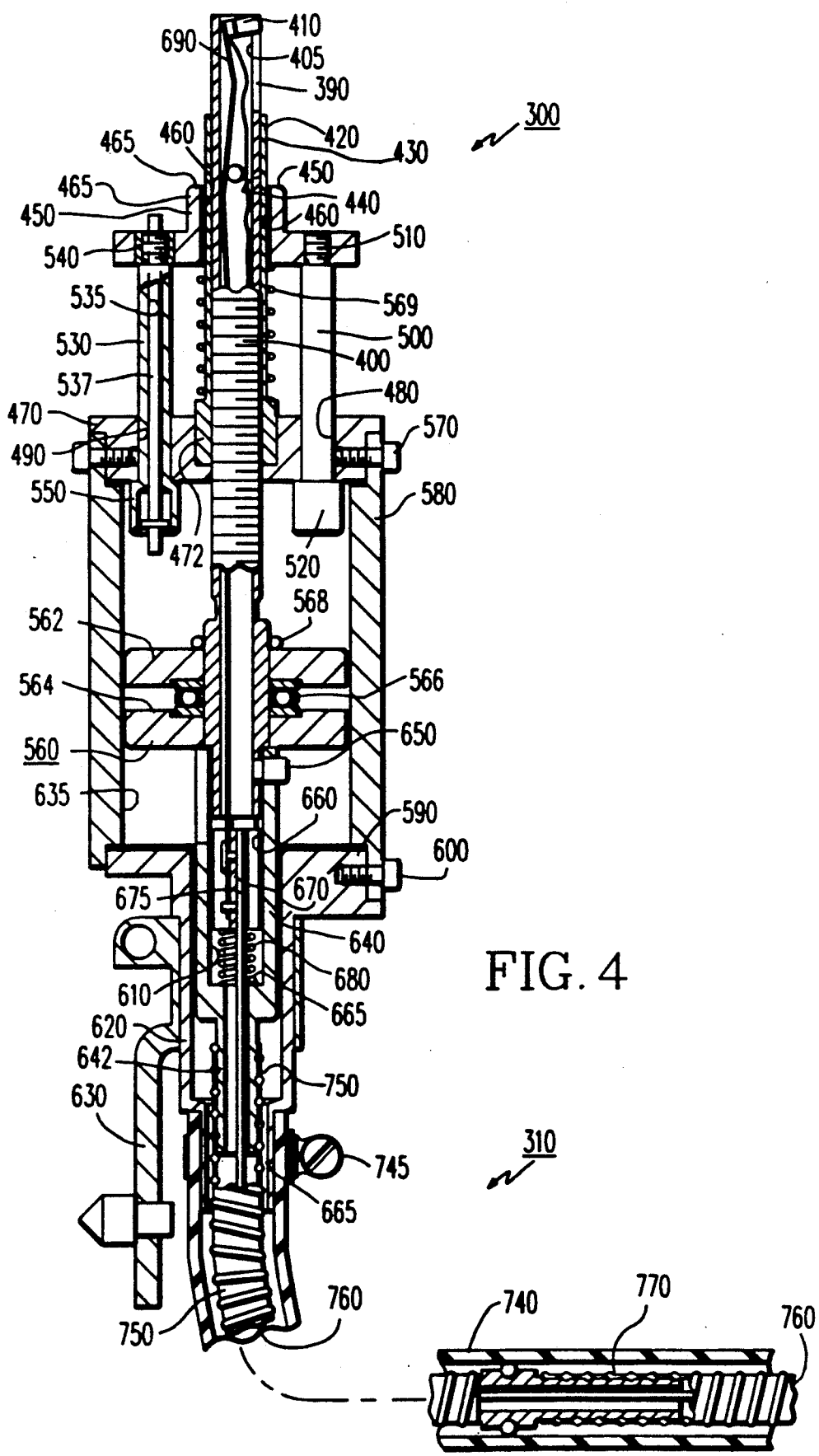
FIG. 4 is a view in partial vertical section of the probe means.
Figure 5:
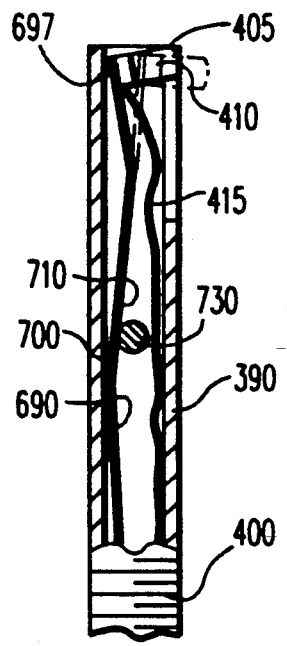
FIG. 5 is a view in partial vertical section of a rotator, a plate assembly and a probe carrier housing, all belonging to the probe means.
Figure 5:
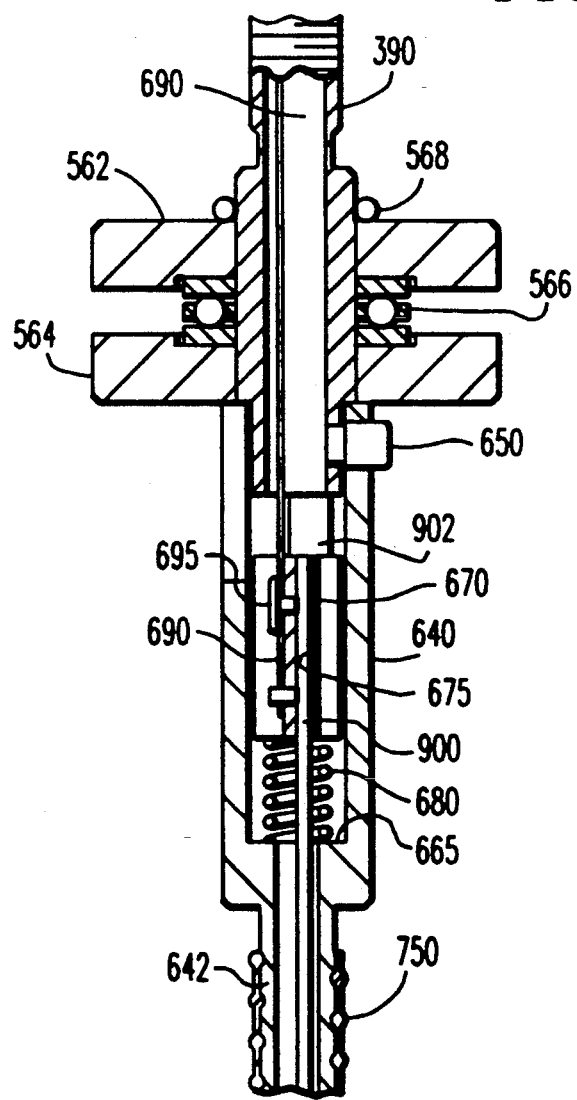
Figure 6:
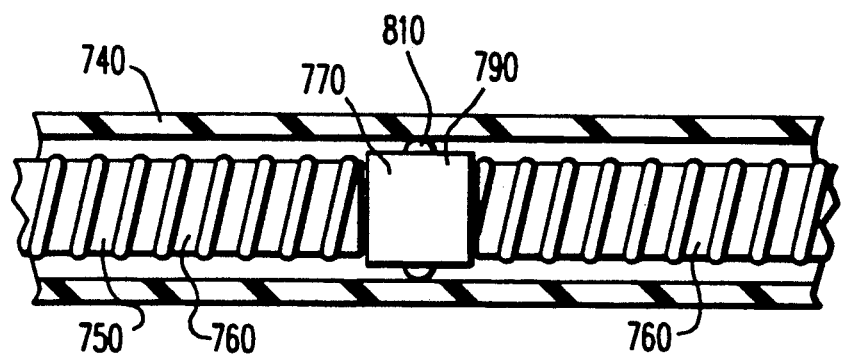
FIG. 6 is a fragmentation view of a conduit having a segmented hose extending therethrough and a connector interposed between adjacent segments of the hose.
Figure 7:
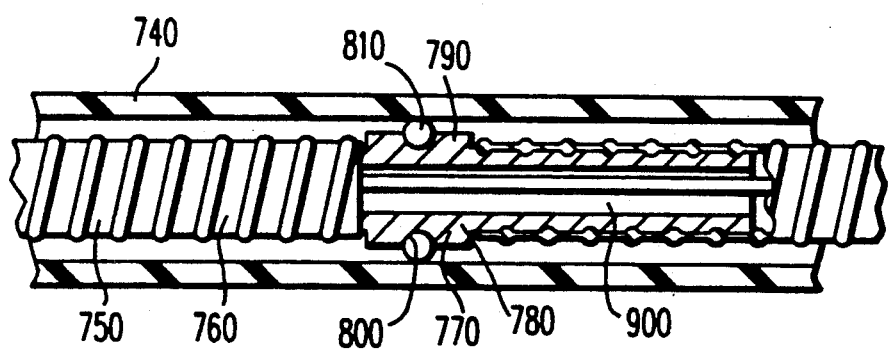
FIG. 7 is a fragmentation view in partial vertical section of the conduit, hose and connector.
Figure 8:
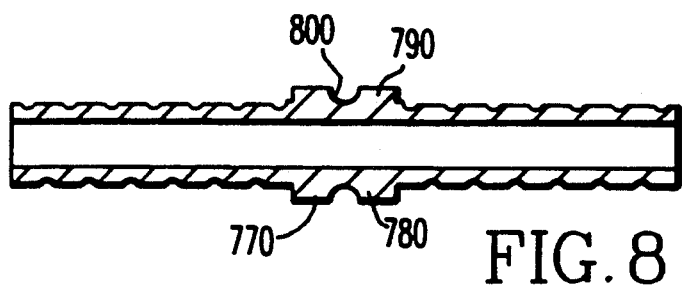
FIG. 8 is a view in vertical section of the body of the connector with parts removed for clarity.

As best seen in FIGS. 3, 4, and 5, a first collar 450 surrounds extension member 430 and has a bore 460 centrally therethrough for slidably receiving extension member 430. First collar 450 has a circular depending shoulder 465 extending around extension member 430, shoulder 465 being sized to abut against open proximal bottom end 360 of tube plug 330. A second collar 470 is spaced apart from first collar 450 and also surrounds extension member 430. Second collar 470 has a step bore 472 therethrough sized to seat the proximal end of extension member 372 in the larger diameter of step bore 472. Moreover, second collar 470 defines a first opening 480 and a second opening 490 for reasons to be described presently. A first guide 500 has a distal end portion 510 thereof anchored in first collar 450 and also has a proximal end portion 520 thereof slidably received in first opening 480 which is formed through second collar 470. A second guide 530 has a distal end portion 540 thereof anchored in first collar 450 and also has a proximal end portion 550 thereof slidably received in second opening 490 which is formed through second collar 470. Second guide 530 has a bore 535 therethrough and an elongated indicator pin 537 extending slidably through bore 535 for reasons disclosed hereinbelow. Moreover, surrounding extension member 430 and adjustably connected thereto is a plate assembly generally referred to as 560. Plate assembly 560 is spaced-apart by a predetermined distance from second collar 470. Plate assembly 560 may comprise a pair of horizontally disposed spaced apart disk-shaped plates 562 and 564. Interposed between plates 562 and 564 is a thrust bearing 566. Surrounding extension member 430 and mounted atop plate 562 is an O-shaped ring member 568 for maintaining plate 562 pressed against thrust bearing 566. Moreover, interposed between first collar 450 and second collar 470 is a resilient spring member 569 for biasing first collar 450 upwardly so that first collar 450 and second collar 470 are maintained in a variable spacedapart relationship and so that shoulder 465 is biased into abutment against open end 360 of tube plug 330.

Still referring to FIGS. 3, 4 and 5, connected to second collar 470 by a plurality of screws 570 is a generally cylindrical casing 580 extending around plate assembly 560 for housing plate assembly 560. Casing 580 has an open distal end which is covered by second collar 470 and an open proximal end which is covered by a closure member 590. Closure member 590 is attached to casing 580 such as by one or more screws 600. Moreover, closure member 590 has a bore 610 therethrough which may be a step bore. Closure member 590 also has an extended portion 620 (which includes bore 610) integrally formed therewith for receiving a connection member 630 which is removably attached to extended portion 620. Connection member 630 is capable of being connected to a positioning device (not shown) for suitably coaxially aligning probe assembly 300 beneath tube plug 330 and for maintaining probe assembly 300 in abutment with tube plug 330 as tube plug 330 is inspected by inspection system 290. The positioning device may be a remotely operated robotic device such as an SM-10W robot available from Westinghouse Electric Corporation located in Pittsburgh, Pa. Second collar 470, casing 390, and closure member 590 together define a cavity 635 within probe assembly 300, in which cavity 635 plate assembly 560 is slidably disposed and housed.

Referring yet again to FIGS. 3, 4 and 5, a generally cylindrical rotator 640, slidably disposed in bore 610, is attached to extension member 430 such as by a set screw 650 and extends from bore 610 to abut against plate 564. Rotator 640 has a step bore 660 therethrough defining a ledge 665 in step bore 660 for reasons provided hereinbelow. For reasons disclosed hereinbelow, disposed in bore 660 is a generally cylindrical actuator 670 having a central bore 675 therethrough. Also disposed in bore 660 and interposed between ledge 665 and actuator 670 is a compression spring 680 for upwardly biasing actuator 670. Rotator 640 also has an elongated portion 642 for reasons disclosed hereinbelow.

As best seen in FIG. 5, a resilient elongated leaf spring 690 is attached, such as by a screw 695, to actuator 670. Leaf spring 690 extends from actuator 670 to adjacent slot 405 formed through probe carrier housing 390. A top end portion 697 of leaf spring 690 is formed into a bent or angled leg 700 having a cam surface 710 thereon. Transversely extending through the upper portion of probe carrier housing 390 is a generally cylindrical or rod-like cam 730 for slidably engaging cam surface 710. It will be understood that as leaf spring 690 is caused to retreat downwardly in the manner described hereinbelow, cam surface 710 will slidably engage cam 730 for radially extending sensor probe 410 through slot 405 to inspect wall 375 of tube plug 330. Similarly, as leaf spring 690 is caused to advance upwardly in the manner described hereinbelow, cam surface 710 will slidably disengage cam 730 for radially retracting sensor probe 410 through slot 405 and into probe carrier housing 390 to protect sensor probe 410 from damage.

Turning now to FIGS. 4, 6, 7 and 8, hose means 310 is connected to the probe means 300. Hose means 310 comprises a flexible conduit 740 connected to extended portion 620 by a removable clamp 745. Hose means 310 further comprises a hollow, segmented and flexible hose 750 connected to rotator 640 and disposed through conduit 740 for rotating rotator 640 which in turn rotates probe carrier housing 390. Hose 750 comprises a plurality of segments 760 for flexibility. Interposed between adjacent segments 760 of hose 750 is a connector 770 for maintaining tension in hose 750 so that hose 750 remains tangle-free as hose 750 is rotated in the manner described hereinbelow. Each connector 770 comprises an elongated generally cylindrical body 780 for receiving the opposing ends of adjacent segments 760 thereon. Each connector 770 further comprises an enlarged portion 790 near the middle portion of body 780. Enlarged portion 790 has a recess 800 formed therein for matingly receiving a spherical bearing 810 which slides or rolls on the inner surface of conduit 740 as hose 750 is rotated and translated in conduit 740.

Figure 9:
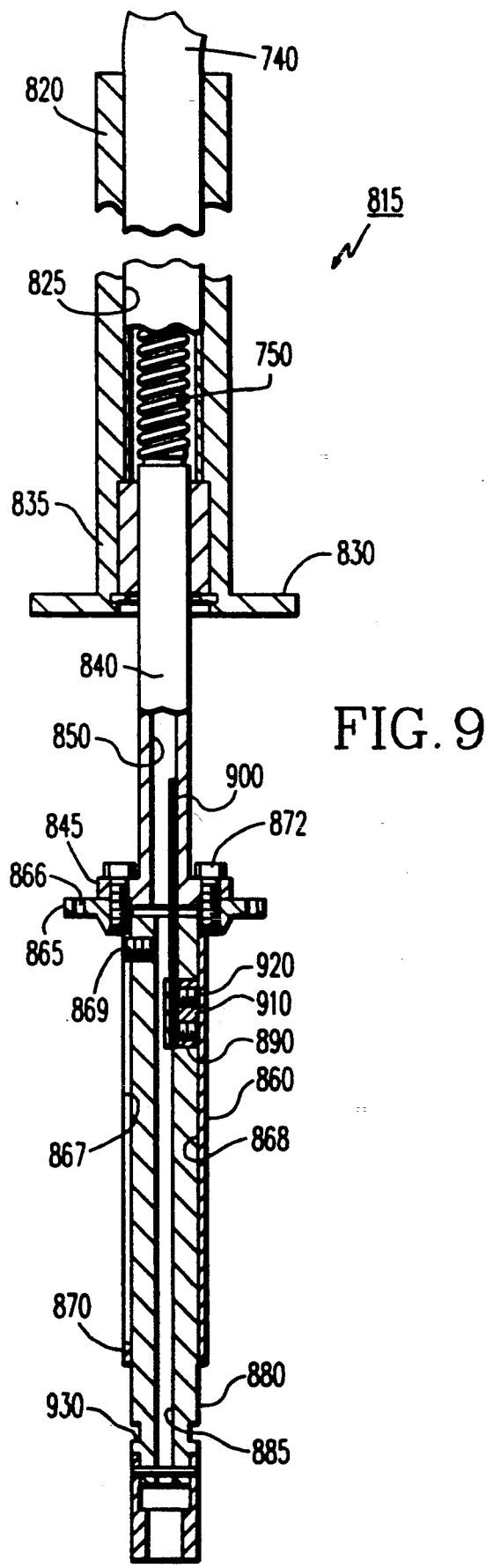
FIG. 9 is a view in partial vertical section of an adaptor assembly for connecting the hose to the drive means.
Figure 10:
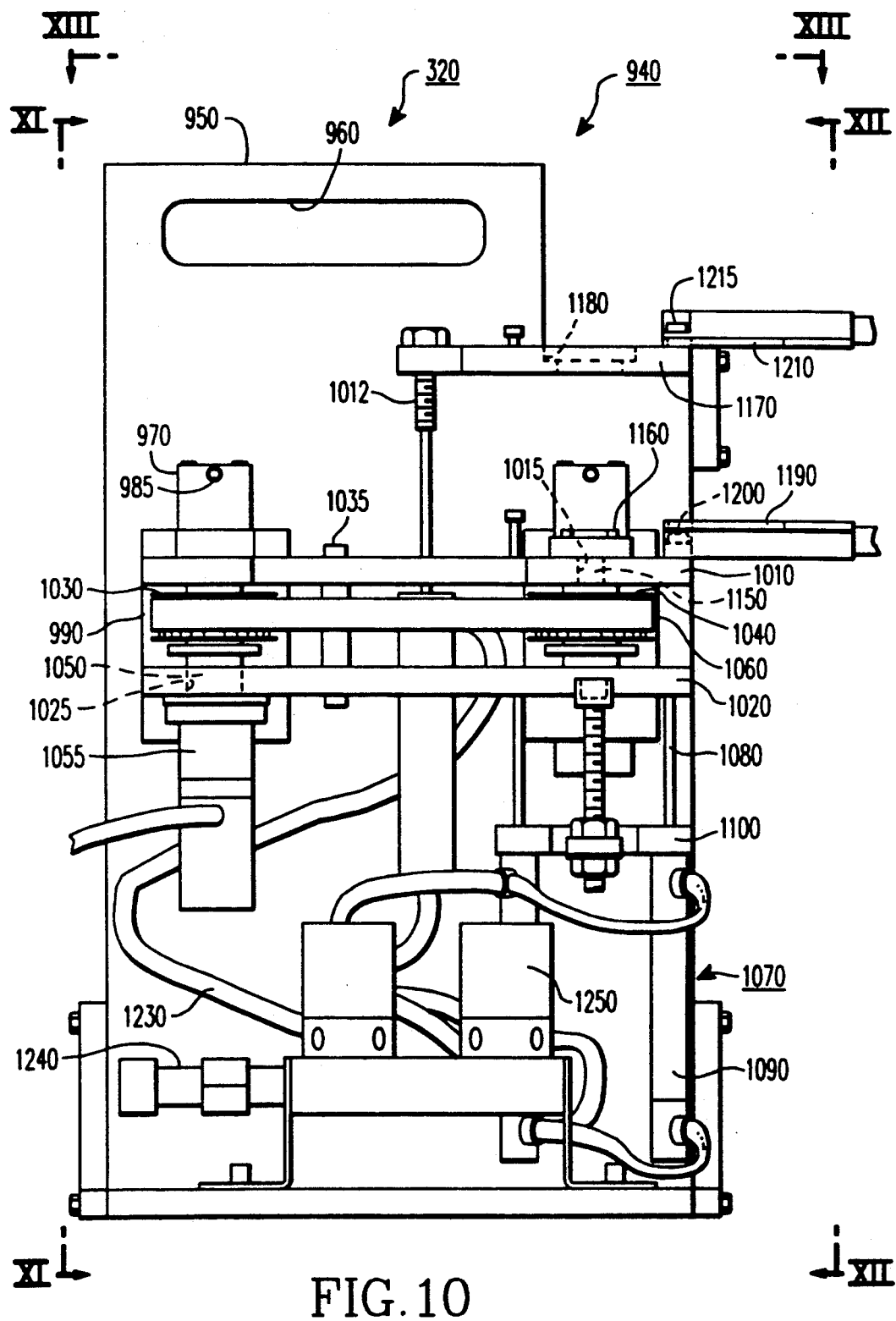
FIG. 10 is a front view of the drive means for driving the inspection probe.
Figure 11:
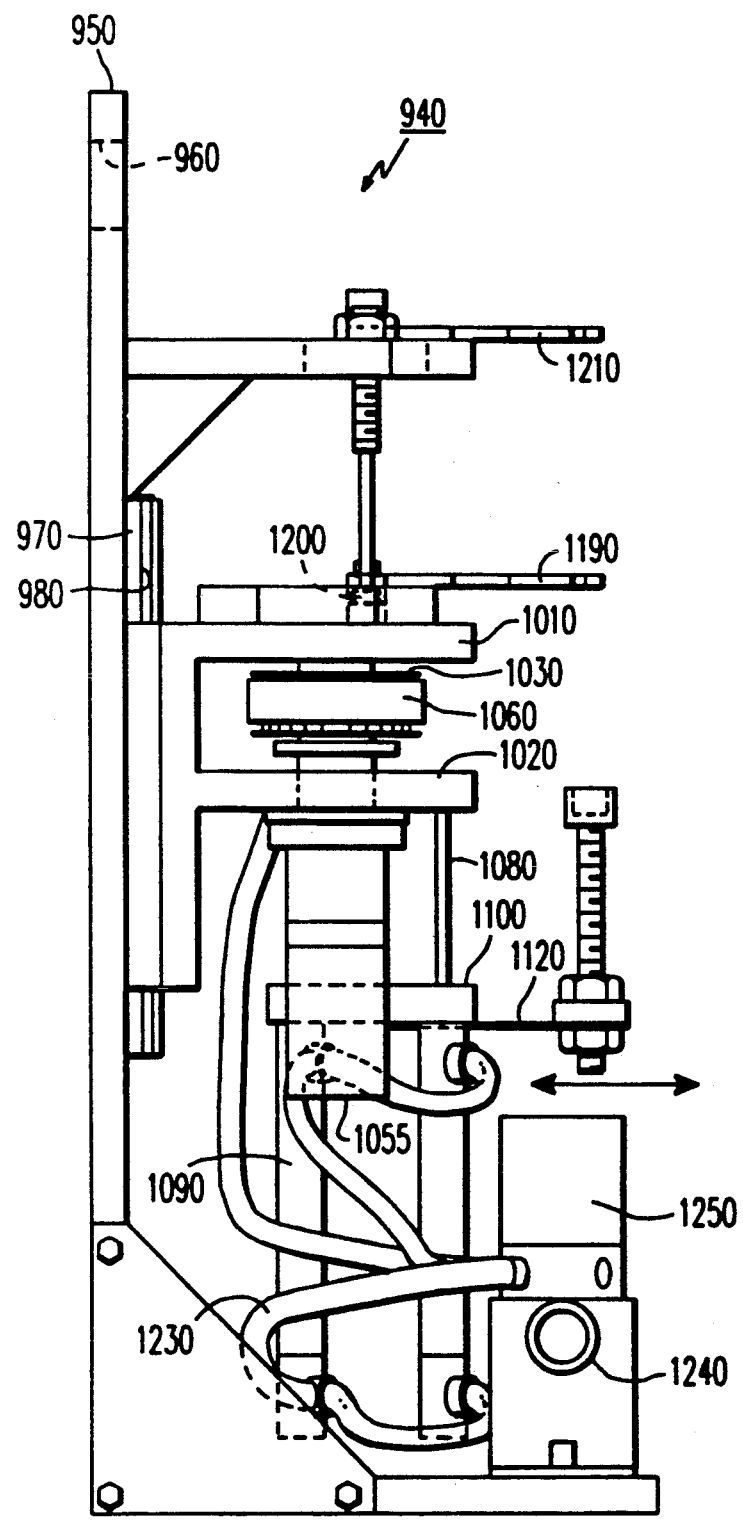
FIG. 11 is a side view of the drive means along section line XI—XI of FIG. 10.
Figure 12:
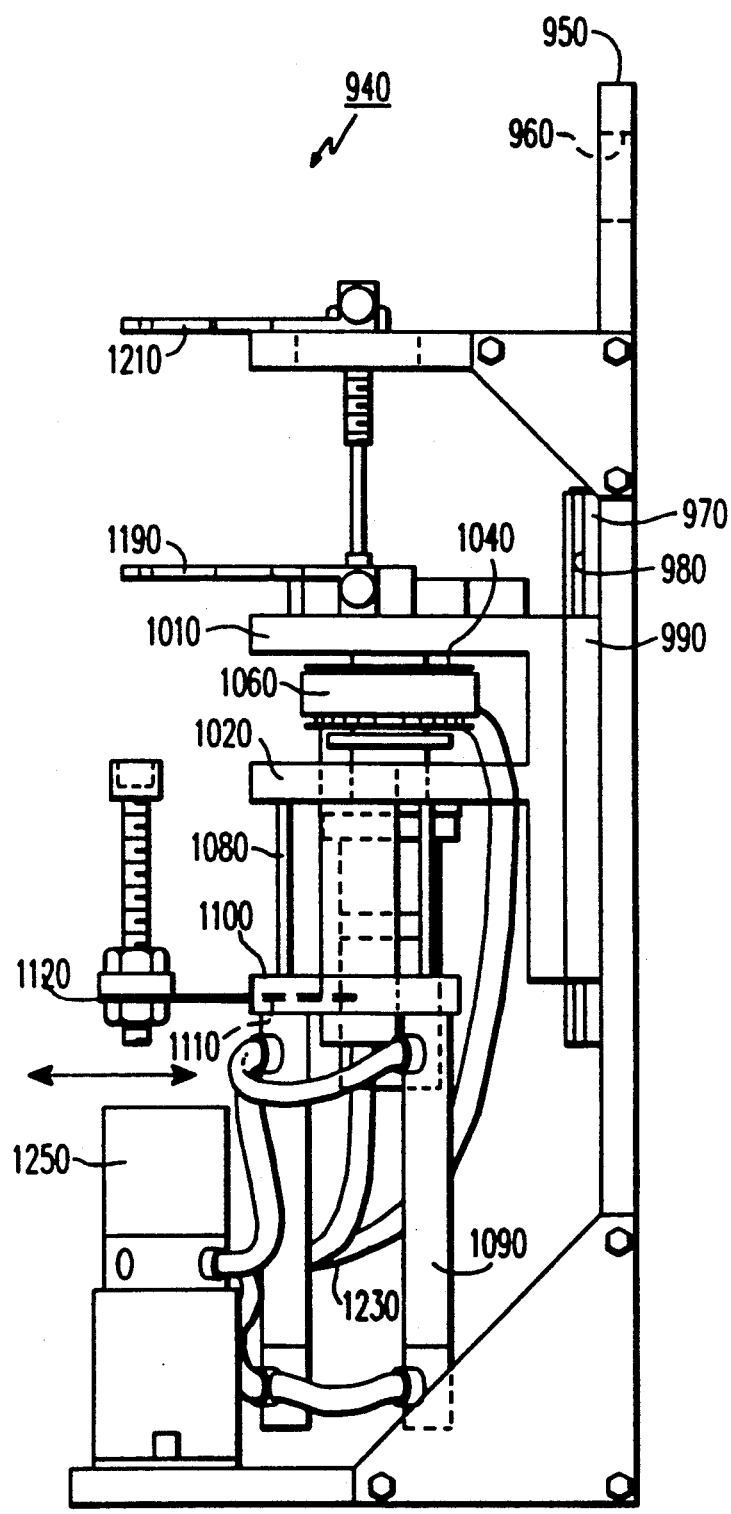
FIG. 12 is another side view of the drive means along section line XII—XII of FIG. 10.

As best seen in FIG. 9, there is shown adaptor means, generally referred to as adaptor assembly 815, for connecting hose means 310 to drive means 320. Adaptor assembly 815 comprises a generally cylindrical barrel 820 having a bore 825 therethrough for receiving conduit 740. Conduit 740 is attached to adaptor assembly 815 in bore 825, such as by a press fit. Barrel 820 also has a flange 830 extending around its proximal end 835 for reasons disclosed hereinbelow. Extending into bore 825 and attached to hose 750 is an elongated generally cylindrical tube nozzle 840 which has a bore 850 therethrough. Tube nozzle 840 terminates in a flange 845 for reasons provided hereinbelow. Attached to tube nozzle 840 is an elongated generally cylindrical slide tube 860 having a circular flange 865 surrounding the distal end thereof, a longitudinal groove 867 therein, and a bore 868 longitudinally therethrough. Flange 865 has a pair of holes 866 transversely therethrough for reasons disclosed hereinbelow. Moreover, slide tube 860 defines a stop 870 at the bottom of qrove 867 for stopping the longitudinal travel of a dowel pin 869. Extending through flange 845 and flange 865 are a plurality of screws 872 for attaching slide tube 860 to tube nozzle 840. Slidably disposed in bore 868 is an elongated cylindrical slide 880 having a bore 885 therethrough, which bore 885 defines a ledge 890 in slide 880. Slide 880 also has a dowel pin 869 attached transversely thereto and sized to slide longitudinally in groove 867.

Still referring to FIG. 9, an elongated flexible cable 900 extends from near ledge 890 through bore 850, through hose 760 to actuator 670. An end of cable 900 is suitably connected to actuator 670, such as by a bolt 902 (see FIG. 5). As shown in FIG. 9, the other end of cable 900 is anchored in a cable holder 910 by a plurality of set screws 920. Formed in the bottom portion of slide 880 is a recessed slot 930 for reasons disclosed hereinbelow.

FIGS. 10, 11, 12, 13 and 14 illustrate drive means 320, such as a probe driver assembly 940, which is capable of receiving adaptor assembly 815. Probe driver assembly 940 comprises a frame 950 having a hole 960 therethrough sized to receive a suitable hoisting tool (not shown) for transporting or carrying probe driver assembly 940. Attached to frame 950 is a flat rectangularly-shaped guide rail 970 having a groove 980 extending along the vertical marginal edges thereof. In the preferred embodiment of the invention, frame 950 has two guide rails 970. Each guide rail 970 is attached to frame 950, such as by a plurality of screws 985. Probe driver assembly 940 further comprises a platform 990 that has a flange 1000 (see FIG. 13) for slidably engaging groove 980 formed in each guide rail 970. As shown in FIGS. 10, 11, 12 and 13, attached to platform 990 is a top shelf 1010 having an aperture 1015 for receiving slide 880 therethrough. Moreover, attached to platform 990 is a bottom shelf 1020 also having an aperture for receiving slide 880 therethrough. Also formed through bottom shelf 1020 is a bore 1025 for reasons described hereinbelow. Connected to top shelf 1010 is a pneumatic cylinder 1012 for raising and lowering (i.e., vertically translating) top shelf 1010 and bottom shelf 1020. Bottom shelf 1020 is spaced-apart from top shelf 1010 for receiving a first pulley 1030 and a hollow second pulley 1040 therebetween. Top shelf 1010 and bottom shelf 1020 are connected by a bolt 1035 attached to shelves 1010 and 1020 so that bottom shelf 1020 moves as top shelf 1010 moves. Second pulley 1040 has an uppermost circumferential flange 1042 integrally attached thereto for reasons provided hereinbelow. The upper portion of second pulley 1040 is received through aperture 1015 and the bottom portion of second pulley is received in a step bore 1041 formed through bottom shelf 1020 (see FIG. 15). As seen in FIGS. 10, 11, 12 and 13, first pulley 1030 and second pulley 1040 are each rotatably connected to top shelf 1010 and to bottom shelf 1020. Extending through bore 1025 is a motor shaft 1050 for rotating first pulley 1030. Motor shaft 1050 is attached to first pulley 1030 at one end of motor shaft 1050 and rotatably connected to a variable speed reversible electric motor 1055 at the other end of motor shaft 1050. It will be appreciated that motor 1055 may alternatively be an air operated motor. Extending around first pulley 1030 and second pulley 1040 is a pulley belt 1060 for rotating second pulley 1040 as first pulley 1030 is rotated by motor 1055.

Still referring to FIGS. 10, 11, 12, 13 and 14, attached to bottom shelf 1020 is a pneumatic cylinder assembly, generally referred to as 1070, having pistons 1080 actuable by a plurality of pneumatic cylinders 1090. A brace 1100 is attached to pistons 1080 so that brace 1100 can be raised and lowered by pistons 1080. Brace 1100 has a slot 1110 therethrough for receiving a slide holder 1120 that has an arch-shaped opening 1122 (see FIG. 16) defining a pair of tines 1124 (see FIG. 16) for matingly slidably engaging slot 930 formed in slide 880. Thus, slide holder 1120 is capable of being slidably outwardly moved to disengage slot 930 and slidably inwardly moved to engage slot 930, as shown by the straight arrows in FIGS. 11, 12, 13 and 16.

Referring yet again to FIGS. 10, 11, 12, 13 and 14, spaced above first shelf 1010 and attached to fame 950 is an uppermost shelf 1170 having a step bore 1180 therethrough. Step bore 1180 is sized to matingly receive flange 830 of adaptor assembly 815 in the larger portion thereof and also sized to receive tube nozzle 840 therethrough. Moreover, attached to the top of top shelf 1010 is a pivotable first locking member 1190 for locking slide tube 860 rotatably in place. First locking member 1190 pivots about bolt 1200 and has a semi-circular hole therethrough for matingly receiving flange 865 of slide tube 860. In addition attached to the top of uppermost shelf 1170 is a pivotable second locking member 1210 for locking barrel 820 (of adaptor assembly 815) in place so that barrel 820 will not vertically move during operation of probe driver assembly 940. Second locking member 1210 pivots about bolt 1215 and has a semi-circular hole 1220 therethrough for matingly receiving barrel 820. Second locking member 1210 is pivotable about bolt 1215 in the direction shown by the curved arrow in FIG. 13.

Referring to FIGS. 10, 11, 12, 13 and 14, a plurality of flexible air tubes 1230 are connected to an air nozzle 1240 at one end thereof and connected to pneumatic cylinders 1012 and 1090 at the other end thereof. Air nozzle 1240 is in turn connected to an air supply source (not shown) for supplying compressed air to air nozzle 1240 and thus to air tubes 1230. Attached to frame 950 and to air tubes 1230 is a solenoid valve assembly 1250 for selectively controlling the flow of air through air tubes 1230.

Figure 15:
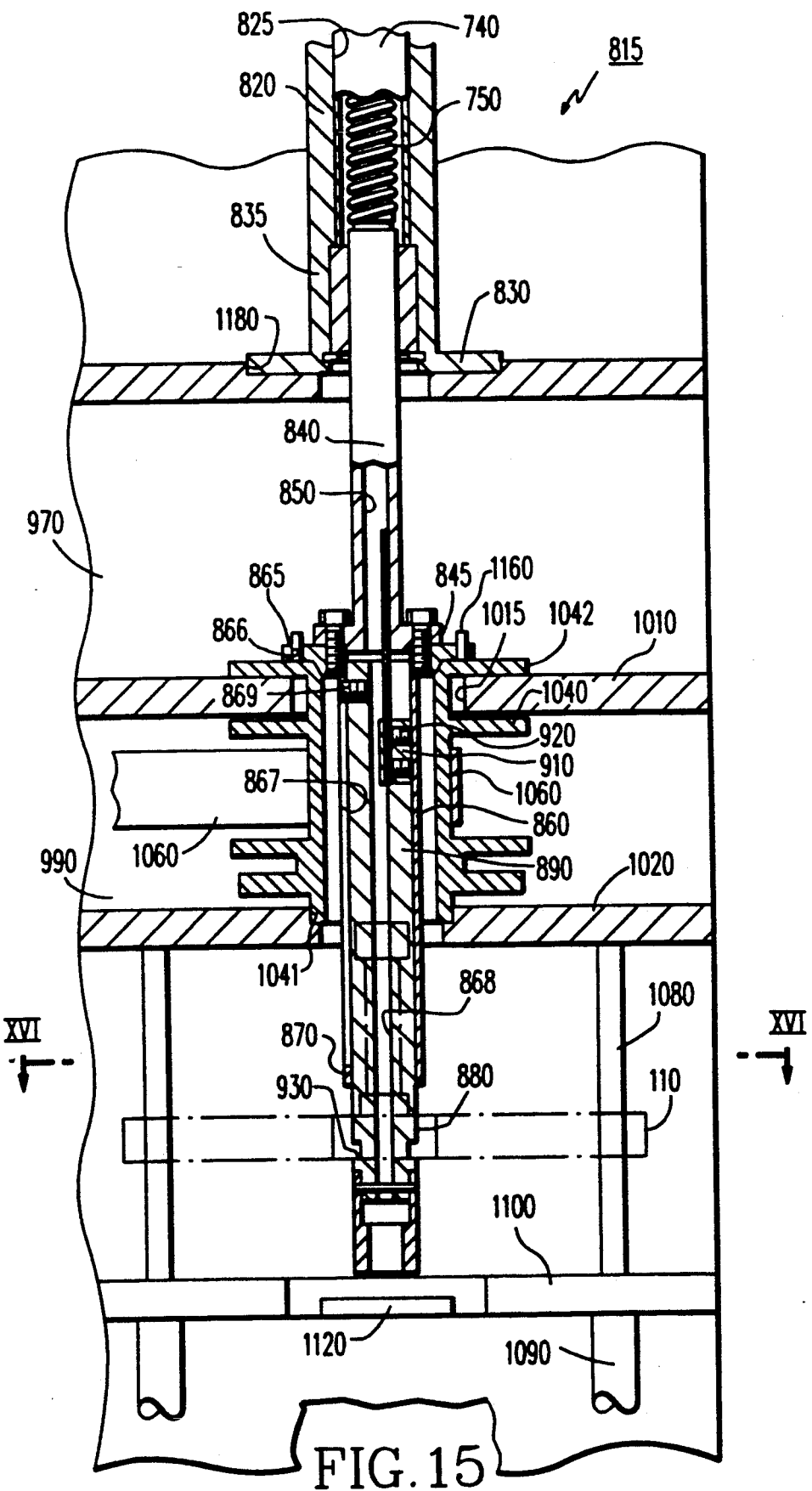
FIG. 15 is a fragmentation view in partial vertical section of the adaptor assembly connected to the drive means.
Figure 13:
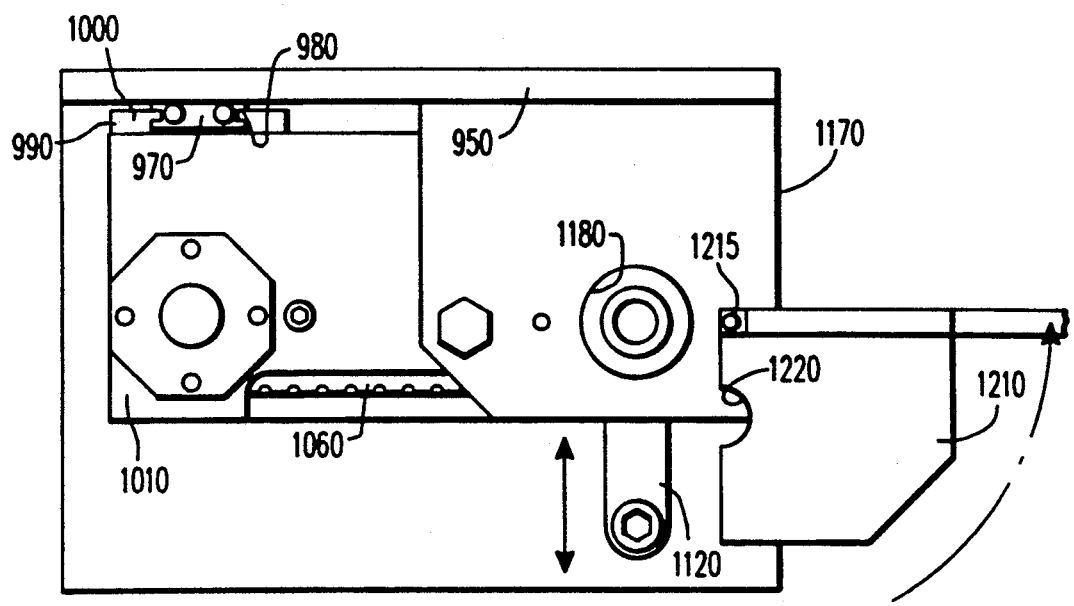
FIG. 13 is a plan view of the drive means along section line XIII—XIII of FIG. 10.
Figure 14:
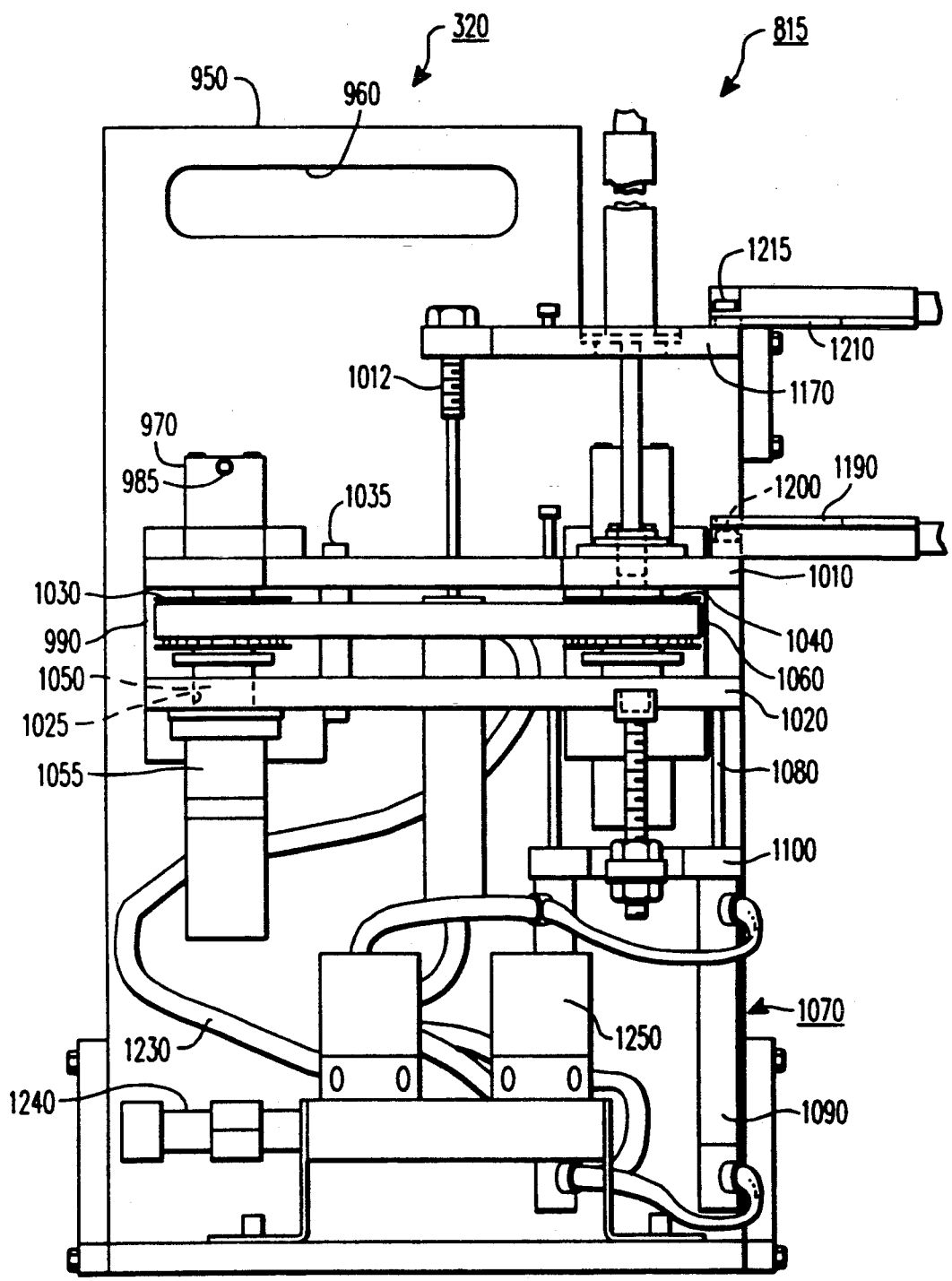
FIG. 14 is a view of the drive means and the adaptor assembly connected thereto.

As best seen in FIGS. 14 and 15, adaptor assembly 815 is connected to drive means 320. When adaptor assembly 815 is connected to drive means 320, flange 830 is received in step bore 1180 of uppermost shelf 1170. Slide tube 860, which also belongs to adaptor assembly 815, is received through hollow second pulley 1040 such that flange 865 of slide tube 860 is mounted on the top surface of second pulley 1040. When flange 865 is mounted on second pulley 1040, ridges 1160, which are integrally attached to second pulley 1040, are matingly received through holes 866 formed in flange 865, which belongs to slide tube 860. Thus, it will be understood that as second pulley 1040 rotates, slide tube 860 will also rotate because ridges 1160 connect slide tube 860 to second pulley 1040.

Figure 16:
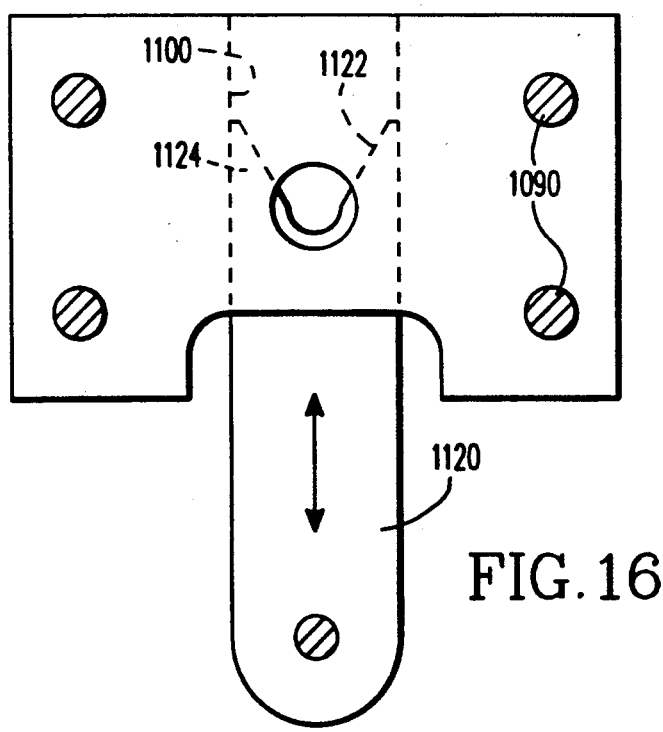
FIG. 16 is a View of a brace along section line XVI—XVI of FIG. 15.

FIG. 16 illustrates brace 1100 having slot 1110 for receiving slide holder 1120. Slide holder 1120 may be selectively moved in the direction of the straight arrow shown in FIG. 16 such that tines 1124 engage or disengage slot 930 formed in slide 880, as disclosed hereinabove.

METHOD OF OPERATION

During operation of inspection system 290, steam generator 10 is taken out of service and the primary and secondary fluids are drained in the customary manner well known in the art. Next, the manway covers (not shown) covering manway opening 75 are removed. One end of hose means 310 is connected to probe assembly 300 by pushing one end of hose 750 onto elongated portion 642 of rotator 640. The other end of hose 750 is attached to tube nozzle 840 which belongs to adaptor assembly 815. A remotely operated robotic device (not shown), such as an SM-10W robotic arm, is connected to probe assembly 300 by connecting the robotic device to connection member 630. The operator of the robotic device causes the robotic device to be inserted through manway opening 75 and operates the robotic device to align probe assembly 300 coaxially beneath the tube plug 330 which is to be inspected.

Frame 950 is transported to near steam generator 10 by engaging a suitable hoisting tool (not shown) into hole 960 belonging to frame 950 and carrying or transporting probe driver 940 to a low-radiation area in the vicinity of steam generator 10. The hoisting tool may then be disengaged from hole 960. Adaptor assembly 815 is connected to probe driver 940 in the manner disclosed immediately hereinbelow. Adaptor assembly 815 is removably connected to probe driver 940 such that flange 830 belonging to end 835 of barrel 820 is matingly received in step bore 1180 (see FIG. 15). As flange 830 is received in step bore 1180, slide 880 will be received through hollow second pulley 1040 and ridges 1160 will be matingly received through holes 866 of slide 880.

Adaptor assembly 815 is then locked to probe driver 320 in the manner described immediately hereinbelow to secure adaptor assembly 300 to probe driver 940. In this regard, first locking member 1190 is pivoted about bolt 1200 such that flange 865 of slide tube 860 is matingly received in the semi-circular hole formed through first locking member 1190. Second locking member 1210 is pivoted about bolt 1215 (in the direction shown by the curved arrow in FIG. 14) such that end 835 of barrel 820 is matingly received through the semi-circular hole formed through second locking member 1190. Slide holder 1120 is slidably horizontally translated in slot 1110 (in the direction of the straight arrows shown in FIGS. 11, 12, 13 and 16), which slot 1110 is formed in brace 1100. Slide holder 1120 is horizontally translated such that tines 1124 belonging to slide holder 1120 slidably engage slot 930 formed in slide 880.

An end of conduit 740, which houses hose 750, is pushed over extended portion 620 of closure member 590, which belongs to probe assembly 300. Conduit 740 is then removably connected to extended portion 620 by clamp 745. Thus, it will be understood that probe assembly 300 is connected to hose means 310, which is in turn connected to adaptor assembly 815. Adaptor assembly 815 itself is connected to drive means 320. Thus, it will be appreciated that inspection system 290 generally comprises probe assembly 300, hose means 310, adaptor assembly 815 and drive means 320.

The robotic device is operated to translate probe assembly 300 upwardly such that shoulder 465 of first collar 450 abuts proximal bottom end 360 of tube plug 330. Spring member 569, which extends around the lower portion of extension member 430, compresses and allows first collar 450 to move controllably axially downwardly as a downward reactive force is exerted by proximal bottom end 360 of tube plug 330. As the robotic device continues to upwardly translate probe assembly 300, the proximal bottom end 360 of tube plug 330 exerts a reactive force against shoulder 465, which belongs to first collar 450. This reactive force against first collar 450 causes first guide 500 and second guide 530 to slide downwardly through first opening 480 and second opening 490, respectively. The robotic device will continue to translate probe assembly 300 upwardly until the top end of extension member 430 abuts the bottom of expander element 380, which is disposed in tube plug 330. In this regard, as first guide 500 and second guide 530 slide downwardly, the distance between the proximal end of indicator pin 537 and plate 562 decreases until extension member 430 abuts expander element 380. The remaining distance between plate 562 and the proximal end of indicator pin 537 equals the length of the interior of tube plug 330 to be inspected. Drive means 320 is then operated in the manner disclosed hereinbelow to upwardly advance plate assembly 560 to close this remaining distance between plate 562 and the proximal end of indicator pin 537. As plate assembly 560 advances upwardly, plate 562, which belongs to plate assembly 560, will abut the proximal end of indicator pin 537 which is slidably disposed through bore 535 of second guide 530. As plate 562 abuts the proximal end of indicator pin 537 and continues to translate vertically upwardly, the distal end of indicator pin 537 will also vertically upwardly translate.

Vertical movement of the distal end of indicator pin 537 indicates that the inspection process is complete because, as disclosed hereinabove, the distance between the proximal end of indicator pin 537 and plate 562 equals the length of the interior of tube plug 330 to be inspected.

As more fully described hereinbelow, operation of motor 1055 upwardly advances plate assembly 560. In this regard, motor 1055 is operated to rotate motor shaft 1050 which in turn rotates first pulley 1030 because motor shaft 1050 is attached to first pulley 1030. As first pulley 1030 rotates, pulley belt 1060 rotates. As pulley belt 1060 rotates, second pulley 1040 also rotates because pulley belt 1060 wraps around both first pulley 1030 and second pulley 1040. Slide 880 rotates as second pulley 1040 rotates because ridges 1160, belonging to second pulley 1040, connect second pulley 1040 to flange 865 which is integrally attached to slide 880. Moreover, as slide 880 rotates, tube nozzle 840 also rotates because tube nozzle 840 is attached to flange 865 by screws 872.

As tube nozzle 840 rotates, segmented hose 750 also rotates because an end of hose 750 is attached to tube nozzle 840 (see FIG. 15). As disclosed hereinbelow, rotation of segmented hose 750 causes segmented hose 750 to travel along the interior of conduit 740. Connector 770, which is interposed between adjacent segments 760 of segmented hose 750, has a plurality of bearings 810 for allowing hose 750 to rotatably slidably travel along the interior of conduit 740. As hose 750 rotates, rotator 640 rotates because hose 750 is connected to elongated portion 642 of rotator 640. Rotation of rotator 640 will cause probe carrier housing 390 to rotate because rotator 640 is attached to probe carrier housing 390 by set screw 650. As described hereinabove, the external threads 400 of probe carrier housing 390 threadably engage the internal threads (not shown) of extension member 430. Therefore, as probe carrier housing 390 is rotated by rotator 640, probe carrier housing 390 will vertically threadably advance in extension member 430 as external threads 400 threadably engage the internal threads of extension member 430. Thus, it will be appreciated that the advancement of hose 750 through conduit 740 also advances probe carrier housing 390 through extension member 430.

Air nozzle 1240 supplies compressed air to pneumatic cylinder 1012 for raising and lowering bottom shelf 1020. Of course, it will be understood that, as bottom shelf 1020 is raised and lowered (i.e., vertically translated), top shelf 1010 is similarly raised and lowered a like distance because bottom shelf 1020 is attached to top shelf 1010 by bolt 1035. As top shelf 1010 and bottom shelf 1020 are thusly translated, platforms 990 are similarly translated because top shelf 1010 and bottom shelf 1020 are attached to platforms 990. As platforms 990 are translated, flange 100, belonging to each platform 990, will matingly slide in grooves 980 formed in each platform 990 so that shelves 1010 and 1020 smoothly slidably move in the vertical direction (i.e., either upwardly or downwardly). The air flow to pneumatic cylinder assembly 1070 and to pneumatic cylinder 1012 is selectively controlled by solenoid valve assembly 1250 in a manner well known in the art. Hence, top shelf 1010, bottom shelf 1020 and brace 1100 are vertically adjustable to receive adaptor assembly 815 and to actuate leaf spring 690.

As probe carrier housing 390 continues to advance in the manner disclosed hereinabove, slot 405 in probe carrier housing 390 will eventually clear extension member 330 and then also clear expander element 380 so that sensor probe 410 can be extended through slot 405 to inspect the upper interior region of tube plug 330. Of course, as probe carrier housing 390 threadably longitudinally translates into tube plug 330, it also transversely rotates in the manner described hereinabove allowing sensor probe 410 to provide a helical inspection scan of tube plug 330 between distal top end 350 and expander element 380.

In the manner described hereinbelow, sensor probe 410 is capable of being extended through slot 405 to inspect tube plug 330. Compressed gas, such as compressed air or the like, is supplied to air nozzle 1240. Air nozzle 1240 supplies the compressed air to air tubes 1230 which conduct the air to pneumatic cylinders 1090 that belong to pneumatic cylinder assembly 1070 which raises and lowers brace 1100. Moving brace 1100 downwardly causes slide 880 to move downwardly a like extent because tines 1124 belonging to brace 1100 engage slot 930 belonging to slide 880. Moving slide 880 downwardly causes cable 900 to move downwardly a like extent because cable 900 is attached to slide 880 at cable holder 910. Moving cable 900 downwardly causes actuator 670 to move slidably downwardly a like extent because cable 900 is attached to actuator 670 by bolt 902. Moving actuator 670 downwardly causes leaf spring 690 to move downwardly because leaf spring 690 is attached to actuator 670 by screw 695. Moving leaf spring 690 downwardly causes cam surface 710, which belongs to leaf spring 690, to slidably engage cam 730. As cam surface 710 slidably engages cam 730, bent leg portion 700 flexes or deflects causing top end portion 697, which has sensor probe 410 attached thereto, to extend radially outwardly toward wall 375 of tube plug 330 for inspecting tube plug 330.

After tube plug 330 is inspected, inspection system 290 is withdrawn from tube plug 330 in a manner substantially the reverse of its insertion into tube plug 330. After tube plug 330 is inspected, inspection system 290 is relocated to inspect another tube plug 330, if desired. After the desired number of tube plugs are inspected, inspection system 290 is removed from steam generator 10 substantially in reverse order of its insertion into steam generator 10. The manway covers (not shown) are replaced over manway openings 75 and steam generator 10 may then be returned to service.

Although the invention is fully illustrated and described herein, it is not intended that the invention as illustrated and described be limited to the details shown, because various modifications may be obtained with respect to the invention without departing from the spirit of the invention or the scope of equivalents thereof. For example, a modification of the present invention would be to eliminate the extension member for suitably inspecting tube plugs not having expander members therein. A further modification of the present invention would be to connect a suitable video camera assembly to probe assembly 300 for viewing the tube plug inspection process.

Although the invention was conceived during an investigation directed towards improving techniques used for examining the interiors of tube plugs and was therefore described in connection with such use, it will be appreciated that the invention may have other uses, such as for examining the interiors of any tubular member or other type of conduit.

Therefore, what is provided is a system for inspecting a tube plug having an expander member disposed therein, wherein the system is capable of inspecting the upper region of the tube plug between the top of the tube plug and the top of the expander member to determine if the upper region of the tube plug is degraded or cracked.

What is claimed is:

1. A system for inspecting a tube plug defining a chamber therein and having an open end in communication with the chamber, the chamber having disposed therein an expander element having a bore therethrough, comprising:
    (a) probe means having a sensor probe connected thereto for inspecting the tube plug, said probe means capable of being connected to the tube plug for extending the sensor probe a predetermined distance into the chamber through the open end of the tube plug;
    (b) means connected to the probe means for rotating and translating the sensor probe within the chamber to provide an inspection scan interiorly of the tube plug, said rotating and translating means including:
        (i) a flexible hose connected to said probe means for translating and rotating said probe means, said hose having a plurality of adjacent segments so that said hose is flexible; and
        (ii) a connector interposed between adjacent segments of said hose for maintaining said hose in a tangle-free state; and
    (c) drive means engaging said rotating and translating means for driving said rotating and translating means.

2. The system according to claim 1, wherein said probe means comprises:
    (a) a probe carrier housing capable of being extended through the open end of the tube plug, into the chamber and through the bore of the expander element, said probe carrier housing having the sensor probe disposed therein for housing the sensor probe and for carrying the sensor probe through the bore of the expander element; and
    (b) limit means connected to said probe carrier housing for delimiting the extent said probe carrier housing is extended through the bore of the expander element.

3. The system according to claim 2, wherein said probe means further comprises biasing means connected to the sensor probe for biasing the sensor probe radially outwardly from said probe carrier housing to inspect the tube plug and for biasing the sensor probe radially inwardly into said probe carrier housing to protect the sensor probe from damage.

4. The system according to claim 3, wherein said probe means further comprises actuator means connected to said biasing means for actuating said biasing means.

5. The system according to claim 4, wherein said rotating and translating means comprises
    a cable extending longitudinally through said hose for operating said actuator means, said cable having one end thereof attached to said actuator means.

6. The system according to claim 5, wherein said drive means comprises:
    (a) an adaptor assembly connected to said hose for connecting said hose to said drive means, said adaptor assembly attached to the other end of the cable for moving the cable; and
    (b) means connected to said hose and to the cable for rotating said hose so that said probe carrier housing is rotated and for moving said cable for operating said actuator.

7. A system for inspecting a tube plug capable of being received within a tube for sealing the tube, the tube plug defining a longitudinal axis therethrough and a chamber therein having an expander element disposed in the chamber for expanding the tube plug into sealing engagement with the tube, the expander element having a top surface and a bottom surface thereon and a bore therethrough, the tube plug having a closed end and an open end in communication with the chamber, the tube plug having an upper interior portion between the top end of the tube plug and the top surface of the expander element, comprising:
    (a) a probe assembly abuttable against the open end of the tube plug for extending a sensor probe therefrom through the open end of the tube plug, into the chamber, and through the bore of the expander element, said probe assembly having the sensor probe connected thereto for inspecting the upper interior portion of the tube plug;
    (b) a hose connected to said probe assembly for transversely rotating and longitudinally translating the sensor probe along the longitudinal axis of the tube plug, said hose capable of translating the sensor probe through the bore defined by the expander element for inspecting the upper interior portion of the tube plug, said hose including:
        (i) a plurality of adjacent segments so that said hose is flexible; and
        (ii) a connector interposed between adjacent segments of said hose for maintaining tension in said hose so that said hose is tangle-free; and
    (c) a probe driver assembly connected to said hose for driving said hose.

8. The system according to claim 7, wherein said probe assembly comprises:
    (a) an elongated probe carrier housing connected to said hose and sized to extend through the bore of the expander element, said probe carrier housing having external threads and having the sensor probe disposed therein for housing the sensor probe and for carrying the sensor probe through the bore of the expander element to inspect the upper interior portion of the tube plug, said probe carrier housing having a slot adjacent the sensor probe for passage of the sensor probe therethrough;
    (b) a spring connected to the sensor probe for biasing the sensor probe radially outwardly through the slot of said probe carrier housing to inspect the tube plug and for biasing the sensor probe radially inwardly through the slot of said probe carrier housing to protect the sensor probe from damage; and
    (c) an elongated extension member defining a passage therethrough surrounding said probe carrier housing, the passage having internal threads for threadably engaging the external threads of said probe carrier housing.

9. The system according to claim 8, further comprising limit means connected to said probe assembly for delimiting the extent said probe carrier housing extends through the bore of the expander element.

10. The system according to claim 9, wherein said limit means comprises:
   (a) a first collar slidably surrounding said extension member, said first collar having a shoulder thereon for abutting the open end of the tube plug;
   (b) a second collar spaced apart from said first collar and defining a first opening and a second opening through said second collar, said second collar connected to and surrounding said extension member;
   (c) a spring member surrounding said extension member and interposed between said first collar and said second collar for biasing the shoulder into abutment against the open end of the tube plug;
   (d) an elongated first guide having a distal end portion thereof anchored in said first collar and having a proximal end portion thereof slidably received through the first opening defined by said second collar;
   (e) an elongated second guide having a distal end portion thereof anchored in said first collar and having a proximal end portion thereof slidably received through the second opening defined by said second collar, said second collar having an elongated indicator pin slidably extending therethrough, the indicator pin having a distal end and a proximal end; and
   (f) a plate surrounding and connected to said probe carrier housing, said plate spaced apart by a predetermined distance from the proximal end of the indicator pin.

11. The system according to claim 10, wherein said hose further comprises a cable extending longitudinally through said hose for operating said spring, said cable having one end thereof connected to said spring.

12. The system according to claim 11, wherein said probe driver assembly comprises:
   (a) a frame;
   (b) a guide rail attached to said frame, said guide rail having a groove therein;
   (c) a platform having a flange integrally attached thereto for slidably engaging the groove in said guide rail;
   (d) a shelf attached to said platform; and
   (e) an adaptor assembly connected to said shelf and to said hose for connecting said hose to said shelf.

13. The system according to claim 12, wherein said adaptor assembly comprises:
   (a) a slide tube;
   (b) a pulley rotatably engaging said slide tube for rotating said slide tube;
   (c) a motor engaging said pulley for rotating said pulley;
   (d) whereby as said pulley is rotated by said motor, said slide tube and said hose rotate for rotating said probe carrier housing;
   (e) whereby as said probe carrier housing rotates, said probe carrier housing threadably engages said extension member for rotatably threadably translating said probe carrier housing through the passage defined by said extension member so that said probe carrier housing rotatably translates through the open end of the tube plug, into the chamber and through the bore of the expander element;
   (f) whereby as said probe carrier housing rotatably translates through the bore of the expander member, the sensor probe rotatably translates for providing a helical inspection scan of the upper interior portion of the tube plug; and
   (g) whereby as said probe carrier housing translates, said plate translates and abuts the proximal end of the indicator pin for pushing the indicator pin through said second guide for delimiting the extent of insertion of said probe carrier housing into the tube plug.

14. The system according to claim 13, wherein the cable belonging to said hose has one end thereof connected to said adaptor assembly and the other end thereof connected to said spring for actuating said spring.

15. In a nuclear steam generator, a system for inspecting a tubularly-shaped tube plug capable of being received within a steam generator tube for sealing the tube, the tube plug defining a longitudinal axis therethrough and a inwardly tapered chamber therein, the tube plug having an exteriorly tapered and generally cylindrical expander element disposed in the chamber for expanding the tube plug into sealing engagement with the tube, the expander element having a top surface and a bottom surface thereon and a cylindrical bore therethrough, the tube plug having a closed distal end and an open proximal end in communication with the chamber, the tube plug having an upper interior portion defined by the top end of the tube plug and the top surface of the expander element, comprising a probe assembly including:
   (a) an elongated generally cylindrical probe carrier housing sized to extend through the bore of the expander element, said probe carrier housing having external threads therearound and having a sensor probe disposed therein for housing the sensor probe and for carrying the sensor probe through the bore of the expander element to inspect the upper interior portion of the tube plug, said probe carrier housing having a longitudinal slot therein adjacent the sensor probe for passage of the sensor probe therethrough, said probe carrier housing having a rounded cam attached thereto adjacent the slot;
   (b) an elongated generally cylindrical extension member defining a passage therethrough surrounding said probe carrier housing, the passage having internal threads for threadably engaging the external threads of said probe carrier housing, said extension member capable of abutting the bottom surface of the expander element;
   (c) a generally cylindrical first collar slidably surrounding said extension member, said first collar having a depending circular shoulder thereon for abutting the open end of the tube plug;
   (d) a generally cylindrical second collar spaced apart from said first collar, said second collar connected to and surrounding said extension member and defining a first opening and a second opening through said second collar;
   (e) a helical spring member surrounding said extension member and interposed between said first collar and said second collar for biasing said first collar into abutment against the open end of the tube plug;
   (f) an elongated generally cylindrical first guide having a distal end portion thereof anchored in said first collar and having a proximal end portion thereof slidably received through the first opening defined by said second collar;
   (g) an elongated generally cylindrical second guide having a distal end portion thereof anchored in said first collar and having a proximal end portion thereof slidably received through the second opening defined by said second collar, said second collar having an elongated indicator pin slidably extending therethrough, the indicator pin having a distal end and a proximal end;

(h) a plate assembly surrounding and connected to said probe carrier housing, said plate spaced apart by a predetermined distance from the proximal end of the indicator pin;

(i) a generally cylindrical rotator connected to said probe carrier housing for rotating said probe carrier housing, said rotator having a step bore therethrough;

(j) a generally cylindrical actuator disposed in the bore of said rotator; and (k) an elongated leaf spring extending longitudinally through said probe carrier housing and having a cam surface thereon adjacent the cam and capable of slidably engaging the cam surface for biasing the sensor probe radially outwardly through the slot of said probe carrier housing to inspect the tube plug and for biasing the sensor probe radially inwardly through the slot of said probe carrier housing to protect the sensor probe from damage, said leaf spring having a proximal end thereof attached to the actuator and a bent distal end thereof having the sensor probe connected thereto, the distal end of the leaf spring disposed adjacent the slot of said probe carrier housing for biasing the sensor probe through the slot.

16. The system according to claim 15, further comprising a flexible hose connected to said rotator for rotating said rotator, said hose having a plurality of adjacent segments, said hose including a generally cylindrical connector interposed between adjacent segments of said hose for maintaining tension in said hose so that said hose is tangle-free, said hose having a flexible cable extending therethrough, the cable having a distal end attached to said actuator for operating said actuator;

17. The system according to claim 16, further comprising a probe driver for driving said hose, said probe driver including:
(a) a frame having a vertical leg and a horizontal leg attached to said vertical leg, so that said frame defines an L-shape transverse cross section;
(b) a first guide rail attached to the vertical leg of said frame, said first guide rail having a vertical groove in a marginal edge thereof;
(c) a second guide rail attached to the vertical leg of said frame and spaced apart from said first guide rail, said second guide rail having a vertical groove in a marginal edge thereof;
(d) a first platform slidably engaging said first guide rail, said first platform having a flange integrally attached thereto for slidably engaging the groove in said first guide rail;
(e) a second platform slidably engaging said second guide rail, said second platform having a flange integrally attached thereto for slidably engaging the groove in said second guide rail;
(f) a top shelf attached to said first platform and to said second platform, said top shelf having a step bore therethrough;
(g) a bottom shelf attached to said first platform, to said second platform, and to said top shelf said bottom shelf spaced apart from said top shelf;
(h) a first pulley and a second pulley interposed between and rotatably connected to said top shelf and said bottom shelf, said first pulley having a motor connected thereto for rotating said first pulley, said second pulley having a bore therethrough, said first pulley and said second pulley interconnected by a continuous pulley belt, so that said first pulley and said second pulley rotate as said first pulley is rotated by the motor; and
(i) a pneumatic cylinder connected to said second shelf for raising and lowering said first shelf and said second shelf.

18. The system according to claim 17, wherein said probe driver comprises an adaptor assembly connected to said hose for connecting said hose to said probe driver.

19. The system according to claim 18, wherein said adaptor assembly comprises:
(a) a generally cylindrical barrel having a bore longitudinally therethrough and having a flange surrounding a proximal end thereof so that the flange is matingly receivable in the step bore formed through said top shelf;
(b) a generally cylindrical tube nozzle having a bore longitudinally therethrough and having and end of the hose connected to the distal end of said tube nozzle, said tube nozzle extending outwardly from the bore of said barrel, said tube nozzle having a flange surrounding the proximal end thereof;
(c) a generally cylindrical slide tube extending through the bore of said second pulley, said slide tube connected to said tube nozzle and to said second pulley, for rotating said slide tube as said second pulley rotates and for rotating said tube nozzle as said slide tube rotates so that said hose rotates;
(d) a generally cylindrical slide disposed in the bore of said slide tube, said slide having a bore therein and a circumferential slot extending around the proximal end thereof, said slide having the proximal end of the cable attached thereto for operating the cable;
(e) a brace having a slide holder having tines capable of engaging the slot in said slide; and
(f) a pneumatic cylinder assembly connected to said brace for raising and lowering said brace for operating the cable so that said actuator is actuated;
(g) whereby as said actuator is operated, said leaf spring is operated so that the cam surface slidably engages the cam for outwardly extending the sensor probe to inspect the upper interior portion of the tube plug and inwardly retracting the sensor probe to protect the sensor probe from damage.

* * * * *